US008871222B2

(12) United States Patent
Pugachev et al.

(10) Patent No.: US 8,871,222 B2
(45) Date of Patent: *Oct. 28, 2014

(54) RECOMBINANT *FLAVIVIRUS* VACCINES

(75) Inventors: Konstantin V. Pugachev, Natick, MA (US); Farshad Guirakhoo, Melrose, MA (US); Thomas P. Monath, Harvard, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,153

(22) Filed: Feb. 27, 2012

(65) Prior Publication Data

US 2012/0288520 A1 Nov. 15, 2012

Related U.S. Application Data

(63) Continuation of application No. 11/912,482, filed as application No. PCT/US2006/015241 on Apr. 24, 2006, now Pat. No. 8,124,398.

(60) Provisional application No. 60/674,546, filed on Apr. 25, 2005, provisional application No. 60/674,415, filed on Apr. 24, 2005.

(51) Int. Cl.
*A61K 39/12* (2006.01)
*C12N 7/00* (2006.01)
*C07K 14/005* (2006.01)

(52) U.S. Cl.
CPC ........ *C12N 7/00* (2013.01); *C12N 2770/24162* (2013.01); *C12N 2770/24135* (2013.01); *C07K 14/005* (2013.01); *C12N 2770/24122* (2013.01)
USPC .................................... 424/218.1; 424/202.1

(58) Field of Classification Search
None
See application file for complete search history.

(56) References Cited

U.S. PATENT DOCUMENTS

| | | | | |
|---|---|---|---|---|
| 6,184,024 | B1 | 2/2001 | Lai et al. | |
| 6,676,936 | B1 | 1/2004 | Lai et al. | |
| 6,696,281 | B1 | 2/2004 | Chambers et al. | |
| 6,962,708 | B1 | 11/2005 | Chambers et al. | |
| 7,507,415 | B2 | 3/2009 | Arroyo et al. | |
| 8,124,398 | B2 * | 2/2012 | Pugachev et al. | 435/235.1 |
| 2004/0223979 | A1 | 11/2004 | Chambers et al. | |
| 2005/0053624 | A1 | 3/2005 | Arroyo et al. | |
| 2007/0269458 | A1 | 11/2007 | Guirakhoo et al. | |

FOREIGN PATENT DOCUMENTS

| | | |
|---|---|---|
| JP | 4683926 | 2/2011 |
| WO | WO 93/06214 | 4/1993 |
| WO | WO 98/37911 | 9/1998 |
| WO | WO 01/39802 | 6/2001 |
| WO | WO 02/095075 | 11/2002 |
| WO | WO 03/059384 | 7/2003 |
| WO | WO 03/092592 | 11/2003 |
| WO | WO 03/103571 | 12/2003 |
| WO | WO 2004/045529 | 6/2004 |
| WO | WO 2006/044857 | 4/2006 |

OTHER PUBLICATIONS

Arroyo et al., "ChimeriVax-West Nile Virus Live-Attenuated Vaccine: Preclinical Evaluation of Safety, Immunogenicity, and Efficacy," J. Virol. 78:12497-12507, 2004.

Arroyo et al., "Molecular Basis for Attenuation of Neurovirulence of a Yellow Fever Virus/Japanese Encephalitis Virus Chimera Vaccine (ChimeraVax-JE)," J. Virol. 75:934-942, 2001.

Bredenbeek et al., "A Stable Full-Length Yellow Fever Virus cDNA Clone and the Role of Conserved RNA Elements in *Flavivirus* Replication," J. Gen. Virol. 84:1261-1268, 2003.

Chambers et al., "Yellow Fever/Japanese Encephalitis Chimeric Viruses: Construction and Biological Properties," J. Virol. 73:3095-3101, 1999.

Durbin et al., "Attenuation and Immunogenicity in Humans of a Live Dengue Virus Type-4 Vaccine Candidate with a 30 Nucleotide Deletion in its 3'-Untranslated Region," Am. J. Trop. Med. Hyg. 65:405-413, 2001.

Kofler et al., "Capsid Protein C of Tick-Borne Encephalitis Virus Tolerates Large Internal Deletions and is a Favorable Target for Attenuation of Virulence," J. Virol. 76:3534-3543, 2002.

Mandl, "*Flavivirus* Immunization with Capsid-Deletion Mutants: Basics, Benefits, and Barriers," Viral Immunol. 17:461-472, 2004.

Mandl et al., "Spontaneous and Engineered Deletions in the 3' Noncoding Region of Tick-Borne Encephalitis Virus: Construction of Highly Attenuated Mutants of a *Flavivirus*," J. Virol. 72:2132-2140, 1998.

Markoff et al., "Derivation and Characterization of a Dengue Type 1 Host Range-Restricted Mutant Virus that is Attenuated and Highly Immunogenic in Monkeys," J. Virol. 76:3318-3328, 2002.

Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," J. Virol. 70:3930-3937, 1996.

Pletnev, "Infectious cDNA Clone of Attenuated Langat Tick-Borne *Flavivirus* (Strain E5) and a 3' Deletion Mutant Constructed from it Exhibit Decreased Neuroinvasiveness in Immunodeficient Mice," Virol. 282:288-300, 2001.

Pletnev et al., "Molecularly Engineered Live-Attenuated Chimeric West Nile/Dengue Virus Vaccines Protect Rhesus Monkeys from West Nile Virus," Virol. 314:190-195, 2003.

Pugachev et al., "Traditional and Novel Approaches to *Flavivirus* Vaccines," Int. J. Parasitol. 33:567-582, 2003.

Whitehead et al., "A Live, Attenuated Dengue Virus Type 1 Vaccine Candidate with a 30-Nucleotide Deletion in the 3' Untranslated Region is Highly Attenuated and Immunogenic in Monkeys," J. Virol. 77:1653-1657, 2003.

(Continued)

*Primary Examiner* — Stacy B Chen
(74) *Attorney, Agent, or Firm* — Clark & Elbing LLP

(57) ABSTRACT

The invention provides recombinant flavivirus vaccines that can be used in the prevention and treatment of flavivirus infection. The vaccines of the invention contain recombinant flaviviruses including attenuating mutations.

19 Claims, 8 Drawing Sheets

(56) References Cited

OTHER PUBLICATIONS

Extended European Search Report from European Patent Application No. EP 06751075, dated Jun. 23, 2009 (search completed Jun. 8, 2009).

International Preliminary Report on Patentability from International Application No. PCT/US06/015241 dated Oct. 30, 2007.

International Search Report from International Application No. PCT/US06/015241 dated Aug. 17, 2006.

Search Report from Singapore Patent Application No. 200717147-3, dated Mar. 10, 2010 (date of completion of search) and Apr. 20, 2010 (date of mailing of report).

Written Opinion of the International Searching Authority from International Application No. PCT/US06/015241 dated Aug. 17, 2006.

Written Opinion from Singapore Patent Application No. 200717147-3, dated Mar. 10, 2010 (date of completion of search) and Apr. 20, 2010 (date of mailing of report).

Blaney, Jr. et al, "Chemical Mutagenesis of Dengue Virus Type 4 Yields Mutant Viruses Which Are Temperature Sensitive in Vero Cells or Human Liver Cells and Attenuated in Mice," *J. Virol*. 75, 20: 9731-9740 (2001).

Gritsun et al., "The Degree of Attenuation of Tick-Borne Encephalitis Virus Depends on the Cumulative Effects of Point Mutations," *J. Gen. Virol*. 82: 1667-1675 (2001).

Kofler et al., "A Novel Principle of Attenuation for the Development of New Generation Live *Flavivirus* Vaccines," *Arch. Virol*. 18:191-200 (2004).

Proutski et al., "Biological Consequences of Deletions Within the 3'-Untranslated Region of Flaviviruses May be Due to Rearrangements of RNA Secondary Structure," *Virus Research* 64: 107-123 (1999).

Proutski et al., "Secondary Structure of the 3'-Untranslated Region of Yellow Fever Virus: Implications for Virulence, Attenuation and Vaccine Development, " *J. Gen. Virol*. 78: 1543-1549 (1997).

* cited by examiner

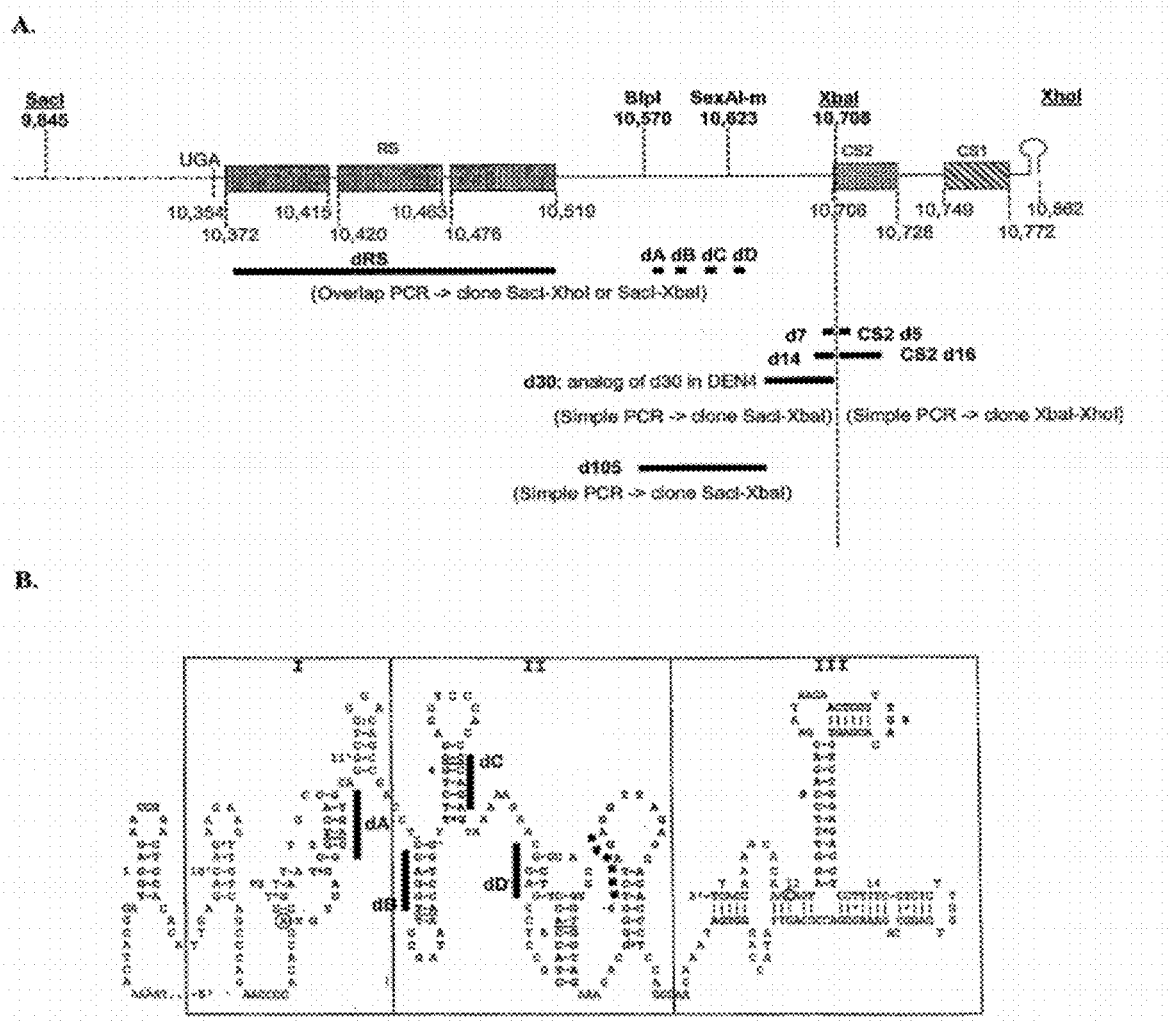

Fig. 1. ...continued
C.
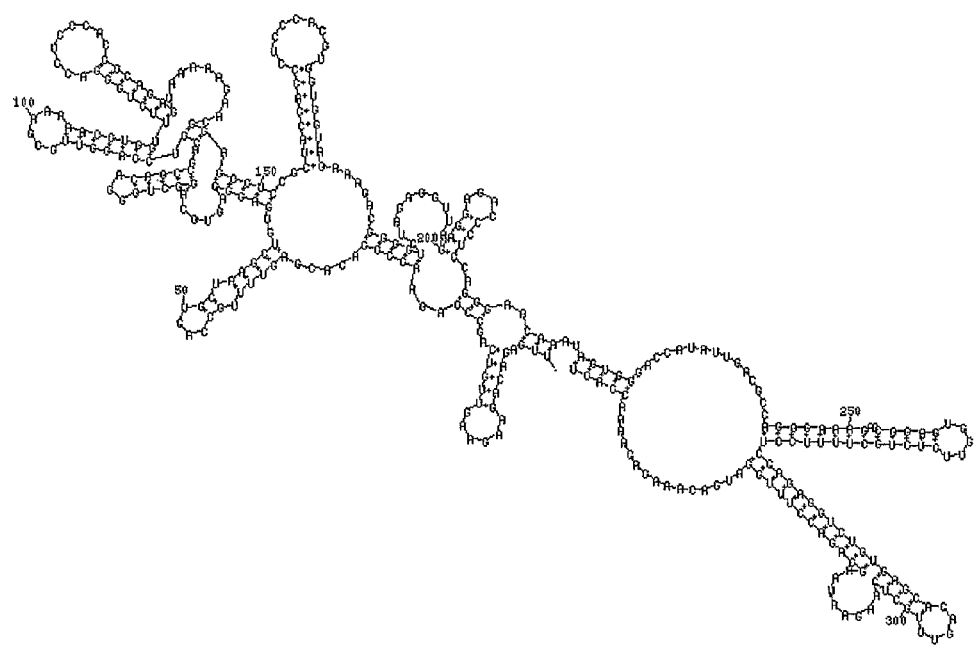

Fig. 1. ...continued
D.
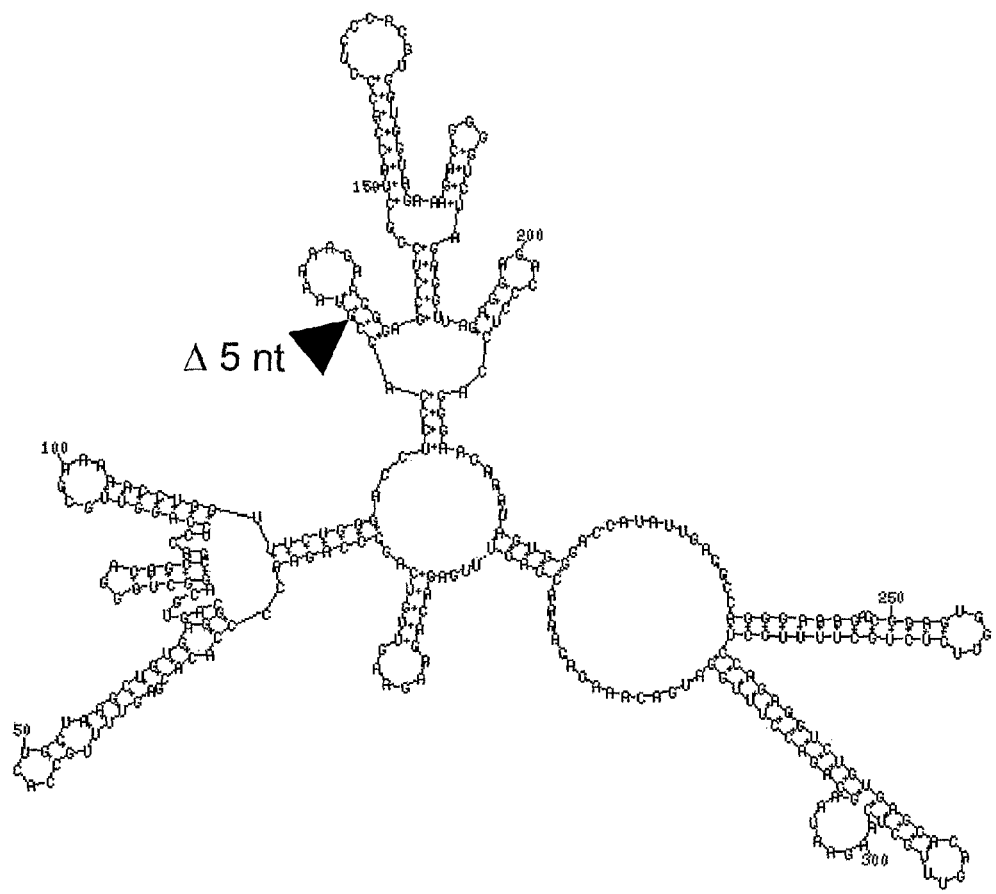
dG = -114.22 [initially -120.5]   dC

Fig. 1. ...continued
E.
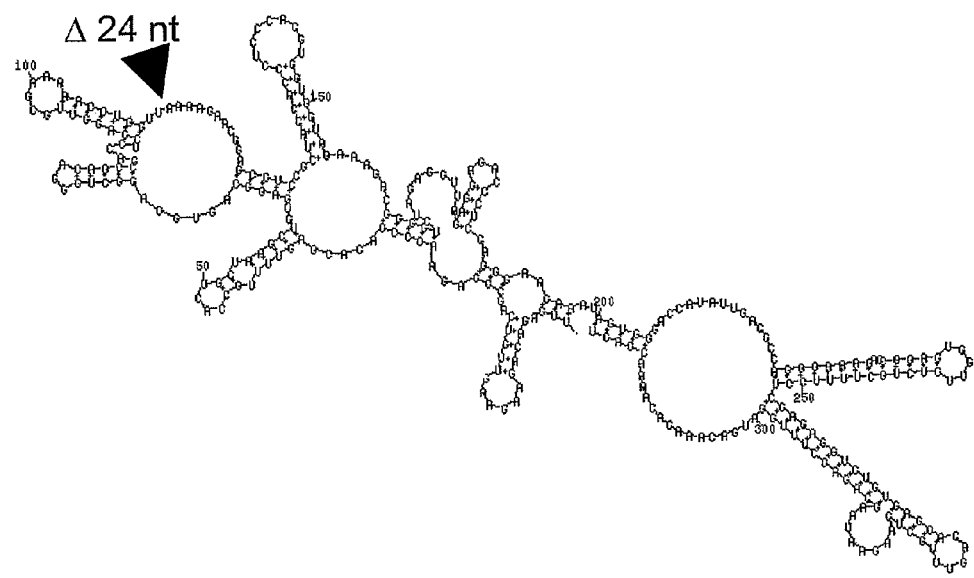
dG = -96.57 [initially -110.6]    dC P5 24nt

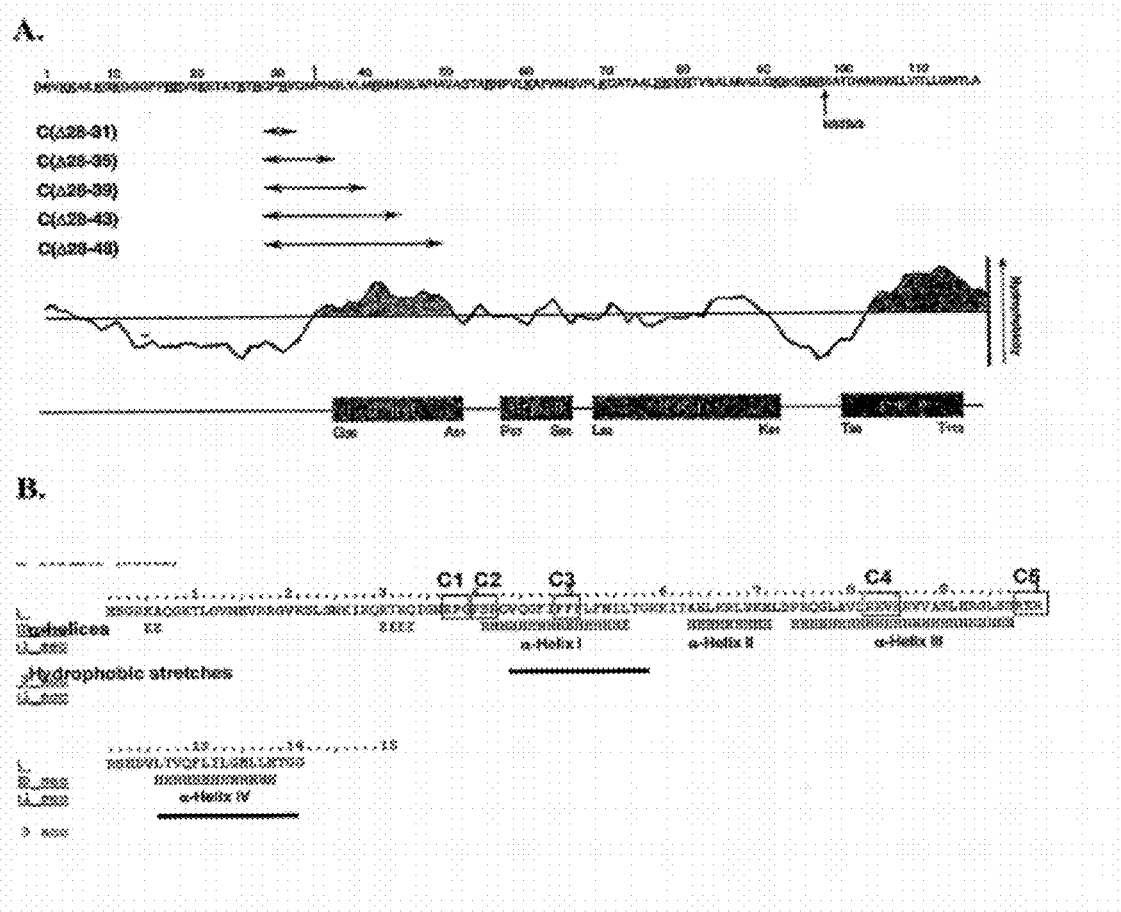

Fig. 4.

SEQUENCE LISTING

```
<160> NUMBER OF SEQ ID NOS: 9

<210> SEQ ID NO 1
<211> LENGTH: 377
<212> TYPE: DNA
<213> ORGANISM: Artificial Sequence
<220> FEATURE:
<223> OTHER INFORMATION: Derived from Yellow fever virus

<400> SEQUENCE: 1
taaaaactac ggatggagaa ccggactcca cacattgaga cagaagaagt tgtcagccca      60 gaacccaca cgagttttgc cactgctaag ctgtgaggca gtgcaggctg ggacagccga     120
cctccaggtt gcgataaacc tggtttctgg gacctccac cccagagtaa aagaacgga     180
```

```
gcctccgcta ccaccttccc acgtggtggt agaaagacgg ggtctagagg ttagaggaga      240
ccctccaggg aacaaatagt gggaccatat tgacgccagg gaaagaccgg agtggttctc      300
tgcttttcct ccagaggtct gtgagcacag tttgctcaag aataagcaga cctttggatg      360
acaaacacaa aaccact                                                    377

<210> SEQ ID NO 2
<211> LENGTH: 343
<212> TYPE: RNA
<213> ORGANISM: Artificial Sequence
<220> FEATURE:
<223> OTHER INFORMATION: Derived from Yellow Fever virus

<400> SEQUENCE: 2
uugagacaga agaaguuguc agcccagaac cccacacgag uuuugccacu gcuaagcugu       60
gaggcagugc aggcugggac agccgaccuc cagguugcga aaaaccuggu uucugggacc      120
ucccacccca gaguaaaaag aacggagccu ccgcuaccac ccucccacgu ggguguagaa      180
agacgggguc uagagguuag aggagacccu ccagggaaca aauaguggga ccauauugac      240
gccagggaaa gaccggagug guucucugcu uuuccuccag aggucuguga gcacaguuug      300
cucaagaaua agcagaccuu uggaugacaa acacaaaacc acu                       343

<210> SEQ ID NO 3
<211> LENGTH: 338
<212> TYPE: RNA
<213> ORGANISM: Artificial Sequence
<220> FEATURE:
<223> OTHER INFORMATION: Derived from Yellow Fever virus

<400> SEQUENCE: 3
uugagacaga agaaguuguc agcccagaac cccacacgag uuuugccacu gcuaagcugu       60
gaggcagugc aggcugggac agccgaccuc cagguugcga aaaaccuggu uucugggacc      120
ucccaccgua aaagaacgg agccuccgcu accacccucc cacguggugg uagaaagacg       180 ggucuagag guuagaggag acccuccagg gaacaaauag ugggaccaua uugacgccag       240
ggaaagaccg gagugguucu cugcuuuucc uccagagguc ugugagcaca guuugcucaa      300
gaauaagcag accuuuggau gacaaacaca aaaccacu                             338

<210> SEQ ID NO 4
<211> LENGTH: 319
<212> TYPE: RNA
<213> ORGANISM: Artificial Sequence
<220> FEATURE:
<223> OTHER INFORMATION: Derived from Yellow Fever virus

<400> SEQUENCE: 4
uugagacaga agaaguuguc agcccagaac cccacacgag uuuugccacu gcuaagcugu       60
gaggcagugc aggcugggac agccgaccuc cagguugcga aaaaccuggu uaaaagaacg      120
gagccuccgc uaccacccuc cacguggug guagaaagac gggucuaga gguuagagga       180 gacccuccag ggaacaaaua gugggaccau auugacgcca gggaaagacc ggagugguuc      240
ucugcuuuuc cuccagaggu cugugagcac aguuugcuca agaauaagca gaccuuugga      300
ugacaaacac aaaaccacu                                                  319

<210> SEQ ID NO 5
<211> LENGTH: 116
<212> TYPE: PRT
```

<213> ORGANISM: Tick-borne Encephalitis virus

<400> SEQUENCE: 5

Met Val Lys Lys Ala Ile Leu Lys Gly Lys Gly Gly Gly Pro Pro Arg
1               5                   10                  15

Arg Val Ser Lys Glu Thr Ala Thr Lys Thr Arg Gln Pro Arg Val Gln
            20                  25                  30

Met Pro Asn Gly Leu Val Leu Met Arg Met Met Gly Ile Leu Trp His
        35                  40                  45

Ala Val Ala Gly Thr Ala Arg Asn Pro Val Leu Lys Ala Phe Trp Asn
    50                  55                  60

Ser Val Pro Leu Lys Gln Ala Thr Ala Ala Leu Arg Lys Ile Lys Arg
65                  70                  75                  80

Thr Val Ser Ala Leu Met Val Gly Leu Glu Lys Arg Gly Lys Arg Arg
                85                  90                  95

Ser Ala Thr Asp Trp Met Ser Trp Leu Leu Val Ile Thr Leu Leu Gly
            100                 105                 110

Met Thr Leu Ala
        115

<210> SEQ ID NO 6
<211> LENGTH: 121
<212> TYPE: PRT
<213> ORGANISM: Yellow Fever Virus

<400> SEQUENCE: 6

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly
        115                 120

<210> SEQ ID NO 7
<211> LENGTH: 16
<212> TYPE: DNA
<213> ORGANISM: Artificial Sequence
<220> FEATURE:
<223> OTHER INFORMATION: Derived from Yellow Fever Virus

<400> SEQUENCE: 7
ggttagagga gaccct                                              16

<210> SEQ ID NO 8
<211> LENGTH: 14
<212> TYPE: DNA
<213> ORGANISM: Artificial Sequence
<220> FEATURE:
<223> OTHER INFORMATION: Derived from Yellow Fever virus

```
<400> SEQUENCE: 8
tggtagaaag acgg                                                      14

<210> SEQ ID NO 9
<211> LENGTH: 19
<212> TYPE: DNA
<213> ORGANISM: Artificial Sequence
<220> FEATURE:
<223> OTHER INFORMATION: Derived from Yellow Fever virus

<400> SEQUENCE: 9
tctgggacct cccacccca                                                 19
```

RECOMBINANT *FLAVIVIRUS* VACCINES

BACKGROUND OF THE INVENTION

The invention relates to vaccines that include recombinant flaviviruses.

Flaviviruses are small, enveloped, positive-strand RNA viruses that are generally transmitted by infected mosquitoes and ticks. Several flaviviruses, such as yellow fever, dengue, Japanese encephalitis, tick-borne encephalitis, and West Nile viruses, pose current or potential threats to global public health. Yellow fever virus, for example, has been the cause of epidemics in certain jungle locations of sub-Saharan Africa, as well as in some parts of South America. Although many yellow fever virus infections are mild, the disease can also cause severe, life-threatening illness. The initial or acute phase of the disease state is normally characterized by high fever, chills, headache, backache, muscle ache, loss of appetite, nausea, and vomiting. After three to four days, these symptoms disappear. In some patients, symptoms then reappear, as the disease enters its so-called toxic phase. During this phase, high fever reappears and can lead to shock, bleeding (e.g., bleeding from the mouth, nose, eyes, and/or stomach), kidney failure, and liver failure. Indeed, liver failure causes jaundice, which is yellowing of the skin and the whites of the eyes, and thus gives "yellow fever" its name. About half of the patients who enter the toxic phase die within 10 to 14 days. However, persons that recover from yellow fever have lifelong immunity against reinfection. The number of people infected with yellow fever virus over the last two decades has been increasing, with there now being about 200,000 yellow fever cases, and about 30,000 associated deaths, each year. The re-emergence of yellow fever virus thus presents a serious public health concern.

West Nile (WN) virus has a wide distribution in Africa, the Indian subcontinent, Europe, Ukraine, Russia, Central Asia, and the Middle East (Monath and Heinz, in Virology 3rd ed., Fields et al., eds., Lippincott-Raven, pp. 961-1034, 1995). In 1999, an unprecedented epidemic of encephalitis in humans and horses caused by WN virus occurred in the United States (Enserik, Science 286:1450-1451, 1999). Since then, the virus has become permanently established in the Americas, affecting nearly the entire territory of the U.S. Thus far the record year in terms of morbidity/mortality in the U.S. was 2003, with 9862 reported cases, of which approximately one-third were accompanied by neurological symptoms, and 264 deaths. The human disease varies from mild dengue-like illness to fatal meningoencephalitis, with the most severe illness occurring in the elderly. To date, there is no effective drug treatment against West Nile virus and methods of surveillance and prevention are not significantly impacting the number of cases of human infection. The risks of the virus migrating into South America, as well as epidemics in underdeveloped countries, are extremely high. The development of a safe and effective vaccine will contribute to the control of future epidemics.

Flaviviruses, including yellow fever virus and West Nile virus, have two principal biological properties responsible for their induction of disease states in humans and animals. The first of these two properties is neurotropism, which is the propensity of the virus to invade and infect nervous tissue of the host. Neurotropic flavivirus infection can result in inflammation of and injury to the brain and spinal cord (i.e., encephalitis), impaired consciousness, paralysis, and convulsions. The second of these biological properties of flaviviruses is viscerotropism, which is the propensity of the virus to invade and infect vital visceral organs, including the liver, kidney, and heart. Viscerotropic flavivirus infection can result in inflammation and injury of the liver (hepatitis), kidney (nephritis), and cardiac muscle (myocarditis), leading to failure or dysfunction of these organs.

Neurotropism and viscerotropism appear to be distinct and separate properties of flaviviruses. Some flaviviruses are primarily neurotropic (such as West Nile virus), others are primarily viscerotropic (e.g., yellow fever virus and dengue virus), and still others exhibit both properties (such as Kyasanur Forest disease virus). However, both neurotropism and viscerotropism are present to some degree in all flaviviruses. Within a host, an interaction between viscerotropism and neurotropism is likely to occur, because infection of viscera occurs before invasion of the central nervous system. Thus, neurotropism depends on the ability of the virus to replicate in extraneural organs (viscera). This extraneural replication produces viremia, which in turn is responsible for invasion of the brain and spinal cord.

Fully processed, mature virions of flaviviruses contain three structural proteins, capsid (C), membrane (M), and envelope (E). Seven non-structural proteins (NS1, NS2A, NS2B, NS3, NS4A, NS4B, and NS5) are produced in infected cells. Both viral receptor binding and fusion domains reside within the E protein. Further, the E protein is also a desirable component of flavivirus vaccines, since antibodies against this protein can neutralize virus infectivity and confer protection on the host against the disease. Immature flavivirions found in infected cells contain pre-membrane (prM) protein, which is a precursor to the M protein. The flavivirus proteins are produced by translation of a single, long open reading frame to generate a polyprotein, followed by a complex series of post-translational proteolytic cleavages of the polyprotein, to generate mature viral proteins (Amberg et al., J. Virol. 73:8083-8094, 1999; Rice, "Flaviviridae," In Virology, Fields et al., ed., Raven-Lippincott, New York, Volume I, p. 937, 1995). The virus structural proteins are arranged in the N-terminal region of the polyprotein in the order C-prM-E, while the non-structural proteins are located in the C-terminal region, in the order noted above.

Live vaccines confer the most potent and durable, protective immune responses against disease caused by viral infections. In the case of flaviviruses, the development of a successful vaccine requires that the virulence properties are modified, so that the vaccine virus has reduced neurotropism and viscerotropism for humans or animals. Several different approaches have been used in the development of vaccines against flaviviruses. In the case of yellow fever virus, two vaccines (yellow fever 17D and the French neurotropic vaccine) have been developed by serial passage (Monath, "Yellow Fever," In Plotkin and Orenstein, Vaccines, $3^{rd}$ ed., Saunders, Philadelphia, pp. 815-879, 1999). The yellow fever 17D vaccine was developed by serial passage in chicken embryo tissue, and resulted in a virus with significantly reduced neurotropism and viscerotropism. The French neurotropic vaccine was developed by serial passages of the virus in mouse brain tissue, and resulted in loss of viscerotropism, but retained neurotropism. Indeed, a high incidence of neurological accidents (post-vaccinal encephalitis) was associated with the use of the French vaccine.

Another approach to attenuation involves the construction of chimeric flaviviruses, which include components of two (or more) different flaviviruses. Chimeric flaviviruses have been made that include structural and non-structural proteins from different flaviviruses. For example, the so-called ChimeriVax™ technology employs the yellow fever 17D virus capsid and nonstructural proteins to deliver the envelope proteins (prM and E) of other flaviviruses (see, e.g., Chambers et al., J. Virol. 73:3095-3101, 1999). Indeed, this technology has been used to develop vaccine candidates against dengue viruses, Japanese encephalitis (JE) virus, West Nile virus, and St. Louis encephalitis (SLE) virus (see, e.g., Pugachev et al., in New Generation Vaccines, 3rd ed., Levine et al., eds., Marcel Dekker, New York, Basel, pp. 559-571, 2004; Chambers et al., J. Virol. 73:3095-3101, 1999; Guirakhoo et al., Virology 257:363-372, 1999; Monath et al., Vaccine 17:1869-1882, 1999; Guirakhoo et al., J. Virol. 74:5477-5485, 2000; Arroyo et al., Trends Mol. Med. 7:350-354, 2001; Guirakhoo et al., J. Virol. 78:4761-4775, 2004; Guirakhoo et al., J. Virol. 78:9998-10008, 2004; Monath et al., J. Infect. Dis. 188:1213-1230, 2003; Arroyo et al., J. Virol. 78:12497-12507, 2004; and Pugachev et al., Am. J. Trop. Med. Hyg. 71:639-645, 2004). These are live viral vaccines, which, similar to the YF17D vaccine, elicit strong humoral and cellular immune responses directed against a desired heterologous virus. Based on extensive characterization of ChimeriVax™-JE and dengue vaccines, the main features of ChimeriVax™ vaccines have been observed to include the ability to replicate to high titers in substrate cells (7 $\log_{10}$ pfu/ml or higher), low neurovirulence in weanling and infant mice (significantly lower compared to YF17D), high attenuation in formal monkey tests for neurovirulence and viscerotropism, high genetic and phenotypic stability in vitro and in vivo, inefficient replication in mosquitoes, which is important to prevent uncontrolled spread in nature, and the induction of robust protective immunity in mice, monkeys, and humans following administration of a single dose, without serious post-immunization side effects.

In other approaches to attenuation, mutagenesis of flaviviruses, including chimeric flaviviruses, has been undertaken. Several experimental approaches to attenuation of wild type flavivirus pathogens have been described (see, e.g., reviewed by Pugachev et al., Int. J. Parasitol. 33:567-582, 2003). For example, it has been found that mutations in certain amino acids of the envelope proteins of chimeric flaviviruses including capsid and non-structural proteins of yellow fever virus and membrane and envelope proteins of Japanese encephalitis virus, a dengue virus, or West Nile virus decrease viscerotropism (see, e.g., WO 03/103571 and WO 2004/045529). Another approach, originally applied to wild type dengue-4 virus, involves large deletions of 30 nucleotides or more in the 3' untranslated region (3'UTR; Men et al., J. Virol. 70:3930-3937, 1996; U.S. Pat. No. 6,184,024 B1). One of these deletions, named deletion delta 30 or Δ30, was further studied in the context of wild type dengue-4 and dengue-1 viruses and a dengue-4/WN chimeric virus (Durbin et al., AJTMH 65:405-413, 2001; Whitehead et al., J. Virol. 77:1653-1657, 2003; Pletnev et al., Virology 314:190-195, 2003; WO 03/059384; WO 03/092592; WO 02/095075). Additionally, some of the large 3'UTR deletions (417-616 nucleotides long) introduced into wild type tick-borne encephalitis (TBE) and Langat viruses were found to be highly attenuating in a mouse model (Mandl et al., J. Virol. 72:2132-2140, 1998; Pletnev, Virology 282:288-300, 2001). A limited amount of in vitro data was published for YF17D vaccine virus. Specifically, Bredenbeek and co-authors demonstrated that a large deletion of all three repeat sequence (RS) elements of the 3'UTR (188 nucleotides in length; the location of the RS elements is illustrated in FIG. 1A) or a 25 nucleotide deletion of the conserved sequence element 2 (CS2) did not preclude virus replication in BHK cells, while three other deletions (25-68 nucleotides in length) that affected CS1 or the 3' extreme stem-and-loop were lethal (Bredenbeek et al., J. Gen. Virol. 84:1261-1268, 2003). Others have shown that mutations introduced into the large 3' terminal stem-loop structure of the flavivirus (dengue) 3'UTR resulted in attenuation, while retaining the ability of the virus to immunize the host (Markoff et al., J. Virol. 76:3318-3328, 2002).

A second approach that was described for attenuation of a highly pathogenic wild type TBE virus utilized relatively large deletions in the capsid protein C, as described by Kofler and co-workers, who introduced a series of deletions into the C protein of TBE virus and recovered several viable mutants (Kofler et al., J. Virol. 76:3534-3543, 2002). Specifically, a 16-amino acid deletion in the central hydrophobic domain of the protein (predicted Helix I; see in FIG. 2A) drastically reduced virus replication in BHK cells and significantly decreased neuroinvasiveness in mice. Immunization with this TBE mutant protected mice from challenge with highly pathogenic TBE strain Hypr (>100 $LD_{50}$) (Kofler et al., J. Virol. 76:3534-3543, 2002).

Approved vaccines are not currently available for many medically important flaviviruses having viscerotropic properties, such as West Nile, dengue, and Omsk hemorrhagic fever viruses, among others.

SUMMARY OF THE INVENTION

The invention provides recombinant flaviviruses (e.g., yellow fever viruses or chimeric flaviviruses) that include one or more mutations that provide a small decrease in viscerotropism to an already attenuated flavivirus, as described herein. An example of a chimeric flavivirus included in the invention is one that includes the capsid and non-structural proteins of a first flavivirus (e.g., a yellow fever virus, such as yellow fever virus strain 17D) and the membrane and envelope proteins of a second flavivirus (e.g., a virus selected from the group consisting of Japanese encephalitis, dengue-1, dengue-2, dengue-3, dengue-4, Murray Valley encephalitis, St. Louis encephalitis, West Nile, Kunjin, Rocio encephalitis, Ilheus, Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses). In the case of a chimeric flavivirus including West Nile virus membrane and envelope proteins, the envelope protein can, optionally, include substitutions in envelope amino acids 107, 316, and 440. The mutations of the recombinant flaviviruses of the invention can be, for example, one or more deletions or substitutions.

The mutations of the invention can be located in regions of the recombinant flaviviruses including, e.g., the 3' untranslated region of the recombinant flaviviruses and generally include fewer than 30 nucleotides. As an example of this type of mutation, the mutation can be one that destabilizes a stem structure in the 3' untranslated region of the virus (e.g., a stem structure in a non-conserved region of the 3' untranslated region of the virus) or possible alternative elements of predicted secondary structure or overall structure. As specific examples, the mutation can be any one or more of d7, dA, dB, dC, and dD, as described herein. In other examples, the mutation can include one or more nucleotides of conserved sequence 2 (CS2) and thus can be, for example, CS2 d5 or CS2 d16. In other examples, the mutant flavivirus is adapted to a cell culture substrate, resulting in spontaneous modification of a mutation that it includes (for example, a deletion, such as, e.g., a modification that increases the original 5-nucleotide deletion in the dC mutant to 24 nucleotides; see below) or in a second site mutation, which does not affect attenuation in vivo.

The mutations of the invention can also be introduced into capsid sequences. Such mutations can include, e.g., a deletion of 1-3 amino acids of the capsid protein. As a specific example of such mutations, the mutations can be one or more deletions in Helix I of the capsid protein (e.g., mutation C2, as described herein).

In other examples, the mutations of the invention can include one or more substitutions of envelope amino acids. In one example, such envelope mutations are substitutions in one or more of envelope amino acids 138, 176, 177, 244, 264, and 280, or combinations thereof. Specific examples of such combinations include the following: 176, 177, and 280; 176, 177, 244, 264, and 280; and 138, 176, 177, and 280.

The recombinant flaviviruses of the invention can include mutations in only one of the regions noted above, or in two or all three of these regions. In addition, the recombinant flaviviruses can include one or more mutations in the hinge region of the envelope protein of the flavivirus, and/or a mutation in the membrane protein of the flavivirus. As specific examples of recombinant flaviviruses of the invention, note is made of flaviviruses including the C2 mutation in combination with d7, dB, dD, and/or E#5 (i.e., E176, E177, and E180) mutations (see below), optionally in the context of ChimeriVax™-WN02 (also see below). Additional examples of recombinant flaviviruses including multiple mutations are provided elsewhere herein.

The invention also provides methods of preventing or treating flavivirus infection in subjects (e.g., human or veterinary subjects), involving administering to the subject a vaccine including one or more of the recombinant flaviviruses described herein, as well as pharmaceutical compositions that include such recombinant flaviviruses. Further, the invention includes nucleic acid molecules (e.g., RNA or DNA molecules) that comprise the genomes (or complements thereof) of such recombinant flaviviruses. In addition, the invention includes use of the recombinant flaviviruses described herein in the preparation of inactivated vaccines. Also included in the invention are methods of attenuating flavivirus vaccine candidates, involving introducing into the flavivirus vaccine candidates one or more mutations that reduce the viscerotropism of the flavivirus vaccine candidates, as described herein.

The invention provides several advantages. The viruses subject to the mutations of the invention are live, attenuated flaviviruses that maintain the ability to infect mammalian cells. Because the viruses are infectious, it is important to ensure that they are sufficiently attenuated, so as not to lead to illness in vaccinated subjects. The present invention provides approaches for fine-tuning the attenuation of candidate flavivirus vaccines, thus enabling the production of safe vaccines. The recombinant flaviviruses of the invention are also advantageous, because they are relatively safe as compared to parental and wild-type strains. This feature is advantageous in their use and administration as live, attenuated vaccines, as well as with respect to their preparation and use as inactivated vaccines.

Other features and advantages of the invention will be apparent from the following detailed description, the drawings, and the claims.

BRIEF DESCRIPTION OF THE DRAWINGS

FIG. 1A is a schematic representation of the 3' untranslated region of yellow fever virus, which shows domains within this region (repeat sequences (RS), CS2, CS1, and the 3'-extreme stem-loop structure), as well as examples of mutations of the invention (e.g., dA, dB, dC, dD, d7, d14, CS2 d5, and CS2 d16).

FIG. 1B is a schematic representation of the sequence (SEQ ID NO: 1) and secondary structure of the 3' untranslated region of yellow fever virus from the middle of the $3^{rd}$ RS element and to the end of the UTR (Proutski et al., J. Gen. Virol. 78:1543-1549, 1999).

FIG. 1C is an schematic representation of the optimal YF 17D 3'UTR secondary structure prediction produced using the Zuker RNA folding algorithm (SEQ ID NO: 2).

FIG. 1D is an schematic representation of the effects of 3'UTR deletions (shown for the dC deletion; Zuker method) on the optimal YF 17D structure (compare with FIG. 1C; SEQ ID NO: 3).

FIG. 1E is an schematic representation of the effect of the spontaneous increase of deletion size in dC virus from 5 nucleotides (at P2 level) to 24 nucleotides (at P5 level) on the predicted secondary structure (compare with FIG. 1D and FIG. 1C; SEQ ID NO: 4). The increased deletion size resulted in a structure resembling the original, optimal YF 17D structure.

FIG. 2A is a schematic representation of the sequence of the capsid protein of tick-borne encephalitis virus (SEQ ID NO: 5), as well as deletions in this protein reported by Kofler et al., J. Virol. 76:3534-3543, 2002.

FIG. 2B is a schematic representation of the sequence of the capsid protein of YF17D (SEQ ID NO: Regions predicted by computer analysis to have α-helical secondary structure (α-helices I-IV), as well as hydrophobic regions, are indicated.

FIG. 4 is a schematic representation of the membrane (M) and envelope (E) proteins of West Nile virus, showing different combinations of mutations introduced into these regions using the two-plasmid approach.

DETAILED DESCRIPTION

Figure 3:
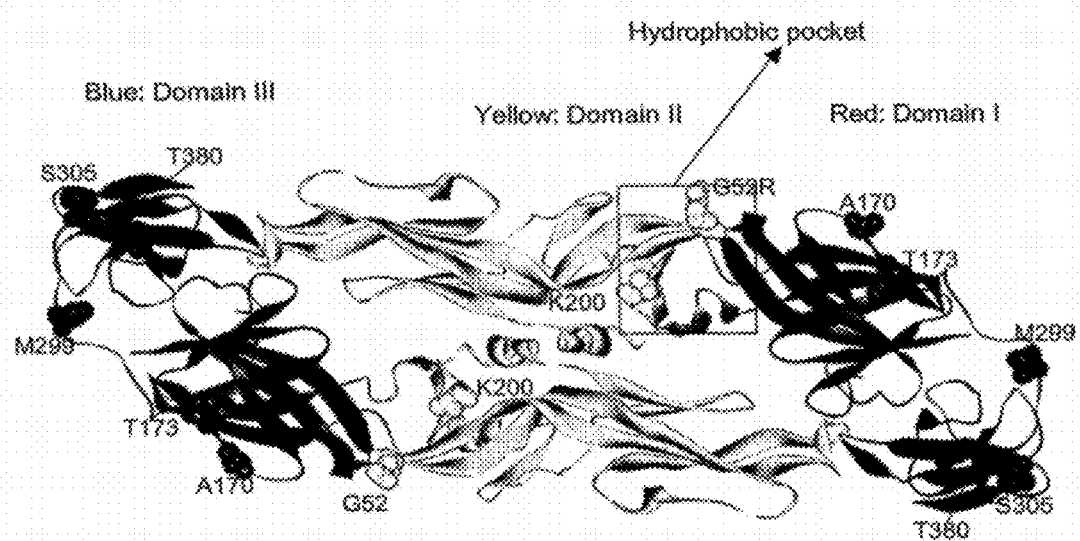
FIG. 3 is a schematic representation of a homology model of the YF E protein homodimer, showing the location of residues that differ between the wild type YF (Asibi) and the vaccine strain YF17D.

The present invention provides recombinant flaviviruses that can be used in therapeutic methods, such as vaccination methods. Central to the flaviviruses of the invention are the presence of attenuating mutations in the genomes of the viruses. These mutations can attenuate the viruses by, for example, decreasing the viscerotropism and/or neurotropism of the viruses. The mutations can be present in regions of the flavivirus genome including the 3' untranslated region (3'UTR), capsid sequences, and/or envelope sequences. As is discussed further below, the mutations of the invention can be used to fine-tune the attenuation of vaccine strains that already include one or more other attenuating mutations. Thus, for example, the mutations of the invention can be identified by resulting in a decrease in plaque size in plaque assays and/or reduced viremia in animal models (see below). The mutations of the invention therefore provide an additional level of safety with respect to the attenuation of such viruses. Details of the viruses and methods of the invention are provided below.

One example of a flavivirus that can be subject to the mutations of the invention is yellow fever virus, for example, the YF17D vaccine strain (Smithburn et al., "Yellow Fever Vaccination," World Health Org., p. 238, 1956; Freestone, in Plotkin et al. (eds.), Vaccines, $2^{nd}$ edition, W. B. Saunders, Philadelphia, 1995). Other yellow fever virus strains, e.g., YF17DD (GenBank Accession No. U 17066) and YF17D-213 (GenBank Accession No. U17067) (dos Santos et al., Virus Res. 35:35-41, 1995), YF17D-204 France (X15067, X15062), YF17D-204, 234 US (Rice et al., Science 229:726-733, 1985; Rice et al., New Biologist 1:285-296, 1989; C 03700, K 02749), and yellow fever virus strains described by Galler et al., Vaccine 16 (9/10):1024-1028, 1998, can also be used in the invention.

Additional flaviviruses that can be subject to the mutations of the invention include other mosquito-borne flaviviruses, such as Japanese encephalitis (e.g., SA14-14-2), dengue (serotypes 1-4), Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Alkhurma, Omsk Hemorrhagic fever, Louping ill, Powassan, Negishi, Absettarov, Hansalova, Apoi, and Hypr viruses; as well as viruses from the Hepacivirus genus (e.g., Hepatitis C virus). All of these viruses have some propensity to infect visceral organs. The viscerotropism of these viruses may not necessarily cause dysfunction of vital visceral organs, but the replication of virus in these organs can cause viremia and thus contribute to invasion of the central nervous system. Thus, in addition to decreasing risk of damage to visceral organs, decreasing the viscerotropism of these viruses by mutagenesis can reduce their abilities to invade the brain and cause encephalitis.

In addition to the viruses listed above, as well as other flaviviruses, chimeric flaviviruses that include one or more of the types of mutations noted above are also included in the invention. These chimeras can consist of a flavivirus (i.e., a backbone flavivirus) in which a structural protein (or proteins) has been replaced with a corresponding structural protein (or proteins) of a second virus (i.e., a test or a predetermined virus, such as a flavivirus; see, e.g., U.S. Pat. No. 6,696,281; U.S. Pat. No. 6,184,024; U.S. Pat. No. 6,676,936; and U.S. Pat. No. 6,497,884). For example, the chimeras can consist of a backbone flavivirus (e.g., a yellow fever virus) in which the membrane and envelope proteins of the flavivirus have been replaced with the membrane and envelope of a second, test virus (e.g., West Nile virus, a dengue virus (serotype 1, 2, 3, or 4), Japanese encephalitis virus, or another virus, such as any of those mentioned herein). The chimeric viruses can be made from any combination of viruses, but typically the virus against which immunity is sought is the source of the inserted structural protein(s).

A specific example of a type of chimeric virus that can be subject to the mutations of the present invention is the yellow fever human vaccine strain, YF17D, in which the membrane protein and the envelope protein have been replaced with the membrane protein and the envelope protein of another flavivirus, such as a West Nile virus, dengue virus (serotype 1, 2, 3, or 4), Japanese encephalitis virus, St. Louis encephalitis virus, Murray Valley encephalitis virus, or any other flavivirus, such as one of those listed above. Chimeric flaviviruses made using this approach have been designated as so-called "ChimeriVax" viruses. The following chimeric flaviviruses, which were made using the ChimeriVax™ technology and deposited with the American Type Culture Collection (ATCC) in Manassas, Va., U.S.A. under the terms of the Budapest Treaty and granted a deposit date of Jan. 6, 1998, can be used to make viruses of the invention: Chimeric Yellow Fever 17D/Dengue Type 2 Virus (YF/DEN-2; ATCC accession number ATCC VR-2593) and Chimeric Yellow Fever 17D/Japanese Encephalitis SA14-14-2 Virus (YF/JE A1.3; ATCC accession number ATCC VR-2594). Details of making chimeric viruses that can be used in the invention are provided, for example, in the following publications: WO 98/37911; WO 01/39802; Chambers et al., J. Virol. 73:3095-3101, 1999; WO 03/103571; WO 2004/045529; U.S. Pat. No. 6,696,281; U.S. Pat. No. 6,184,024; U.S. Pat. No. 6,676,936; and U.S. Pat. No. 6,497,884.

As is noted above, the new mutations of the invention are present in the 3'UTR, capsid, and/or envelope sequences of flaviviruses, including chimeric flaviviruses. Each of these types of mutations, which can be combined with each other and/or other attenuating mutations, are described as follows.

3' Untranslated Region Mutations

The organization of the 3'UTR of a yellow fever virus vaccine strain, YF17D, which is shared by all ChimeriVax™ viruses, is shown in FIG. 1A. It includes in order from the 3' end (i) a 3'-extreme stem-and-loop structure that has been hypothesized to function as a promoter for minus-strand RNA synthesis and is conserved for all flaviviruses, (ii) two conserved sequence elements, CS1 and CS2, which share a high degree of nucleotide sequence homology with all mosquito-borne flaviviruses, and (iii) unique for West African yellow fever virus strains, including the YF17D vaccine virus, three copies of a repeat sequence element (RS) located in the upstream portion of the 3'UTR (Chambers et al., Annu. Rev. Microbiol. 44:649-688, 1990). The 3'UTR also includes numerous predicted stem-loop structures, such as those in the non-conserved region downstream from the RS elements, as depicted in FIG. 1B.

The 3'UTR mutations of the present invention generally are short, attenuating deletions of, for example, less than 30 nucleotides (e.g., 1, 2, 3, etc., and up to 29 (e.g., 2-25, 3-20, 4-15, 5-10, or 6-8 nucleotides in length)). When introduced individually into a vaccine candidate or combined with other attenuating mutations, the new mutations of the invention can result in an additional level of attenuation, thus providing an approach to fine-tune the level of attenuation of a vaccine candidate. In some examples, the short 3'UTR deletions of the invention are designed to destabilize the secondary structure of one or more of the predicted stem structures in the 3'UTR and/or overall structure of the 3'UTR. In addition to deletions, mutations in such structures can also include substitutions that similarly result in stem structure destabilization. In certain examples, the stem-loop structures that are subject to the mutations of the invention are present in non-conserved regions of the 3'UTR or in conserved regions that can tolerate such mutations (e.g., in CS2). For example, in the case of the yellow fever virus (e.g., YF17D) 3'UTR, whether in the context of an intact yellow fever virus or a yellow fever virus-based chimera, the stem destabilizing mutations can be present in any one or more of the stem structures shown in FIG. 1B, which shows four examples of such deletions (dA, dB, dC, and dD), which are described further below. Thus, in addition to these specific examples, other examples of 3'UTR mutations in yellow fever virus include mutations that comprise, e.g., 1-2, 3-8, 4-7, or 5-6 nucleotides of the following stem sequences, which are shown in FIG. 1B as read from 5' to 3': TGGAG (SEQ ID NO: 10), CTCCA (SEQ ID NO: 11), GACAG (SEQ ID NO: 12), TTGTC (SEQ ID NO: 13), AGTTT (SEQ ID NO: 14), GGCTG (SEQ ID NO: 15), CAGCC (SEQ ID NO: 16), AACCTGG (SEQ ID NO: 17), TTCTGGG (SEQ ID NO: 18), CTACCACC (SEQ ID NO: 19), GGTGGTAG (SEQ ID NO: 20), GGGGTCT (SEQ ID NO: 21), AGACCCT (SEQ ID NO: 22), AGTGG (SEQ ID NO: 23), and TTGACG (SEQ ID NO: 24).

In addition to stem destabilizing mutations, the mutations of the invention also include other short deletions in the 3'UTR. For example, the invention includes certain mutations that fall within the Δ30 mutation, described above. Thus, for example, the invention includes any viable mutations that are 1, 2, 3, etc., and up to 29 (e.g., 1-25, 2-20, 3-15, 4-14, 5-13, 6-12, 7-11, 8-10, or 9) nucleotides in length within this region. As a specific example, the invention includes deletion d7, in which the following nucleotides from this region in YF17D are deleted: nucleotides 345-351 (AAGACGG (SEQ ID NO: 25); numbering from the 1$^{st}$ nucleotide of the 3'UTR, after the UGA termination codon of the viral ORF; FIG. 1A). Mutations that include deletion of, for example, 1, 2, 3, 4, or 5 additional nucleotides from the 3' or 5' end of this sequence are also included in the invention. In other examples, short deletions in conserved sequences CS1 and CS2 are included in the invention. These mutations can include deletion of, e.g., 1-29, 2-25, 3-20, 4-15, 5-10, or 6-8 nucleotides of these sequences. As two specific examples, which are described further below, nucleotides 360-364 (GGTTA (SEQ ID NO: 26); CS2d5; FIG. 1A) and/or nucleotides 360-375 (GGTTA-GAGGAGACCCT (SEQ ID NO: 7); CS2d16; FIG. 1A) are deleted from CS2 of the YF17D-specific 3'UTR. Mutations that include deletion of, for example, 1, 2, 3, 4, or 5 additional nucleotides from the 3' or 5' end of this sequence are also included in the invention. For other flavivirus 3'UTRs, similar mutations can be made, based on the secondary structures of the 3'UTR's. Predictions of secondary structures of 3'UTR of other flaviviruses have been published, e.g., for dengue, Kunjin, and TBE (see, e.g., Proutski et al., Virus Res. 64:107-123, 1999) and HCV (see, e.g., Kolykhalov et al., J. Virol. 70:3363-3371, 1996). Further, numerous 3'UTR nucleotide sequences for many strains of flaviviruses representing all four major serocomplexes (YF, JE, dengue, and TBE) are available from GenBank. Sequences of additional strains can be determined by virus sequencing. The secondary structures of these sequences can be easily predicted using standard software (e.g., mfold or RNAfold programs) to reveal potential stem-loop structures that can be subject to mutagenesis.

As discussed further below, 3'UTR mutations of the invention can be used to provide further attenuation for already attenuated vaccine candidates. Thus, one or more of the 3'UTR mutations described herein (e.g., d7, dB, dC, and/or dD) can be made to provide a further level of safety to the YF17D yellow fever virus vaccine strain. Optionally, the 3'UTR mutation(s) can be included in this strain with one or more additional attenuating mutations, such as an attenuating mutation in the hinge region of the envelope protein of the virus (e.g., a substitution of any one or more of envelope amino acids 48-61, 127-131, and 196-283, e.g., amino acid 279, or one or more of the envelope amino acids in yellow fever virus corresponding to amino acids 204, 252, 253, 257, 258, and 261 of dengue 1 virus (see, e.g., WO 03/103571); the hinge region of flavivirus envelope proteins is between Domains I and II; see, e.g., Rey et al., Nature 375:291-298, 1995), an amino acid in the membrane protein of yellow fever virus (for example, the membrane helix portion of the membrane protein, e.g., an amino acid corresponding to position 66 of the West Nile virus membrane protein), or any of the capsid or envelope protein mutations described herein (e.g., amino acid substitutions at positions corresponding to West Nile virus amino acids 138, 176, 177, 244, 264, 280, 313, 316, 380, and 440, alone or in combination).

Indeed, it is possible to combine mutations or deletions specified in the 3'UTR with one or more mutations or deletions in the capsid gene (as described below), in the prM gene (e.g., at M5 or M60 of YF-Japanese encephalitis chimeras, or M66 of YF-WN chimeras or surrounding amino acids (see PCT/US2005/037369 and below), or in the E gene at sites known to attenuate flaviviruses. The E gene contains functional domains within which amino acid changes may affect function and thereby reduce virulence, as described by Hurrelbrink and McMinn (Adv. Virus Dis. 60:1-42, 2003). The functional regions of the E protein in which mutations may be inserted that, together with the 3'UTR deletions/mutations described in the present application, may result in an appropriately attenuated vaccine include: a) the putative receptor binding region on the external surface of domain III, b) the molecular hinge region between domains I and II, which determines the acid-dependent conformational changes of the E protein in the endosome and reduce the efficiency of virus internalization; c) the interface of prM/M and E proteins, a region of the E protein that interfaces with prM/M following the rearrangement from dimer to trimer after exposure to low pH in the endosome; d) the tip of the fusion domain of domain II, which is involved in fusion to the membrane of the endosome during internalization events; and e) the stem-anchor region, which is also functionally is involved in conformational changes of the E protein during acid-induced fusion events.

The 3'UTR mutations can also be included in chimeric flavivirus vaccine candidates. In one example, which is described further below, one or more of the 3'UTR mutations described herein is included in a vaccine candidate (referred to herein as ChimeriVax™-WN02) that includes capsid and non-structural proteins of yellow fever virus (YF17D) and membrane and envelope proteins of West Nile virus (NY99), the envelope protein of which already includes attenuating mutations (substitutions at positions 107, 316, and 440; WO 2004/045529; also see below). Thus, the invention includes ChimeriVax™-WN-02 that also includes, for example, the d7, dB, dC, dD, or any other 3'UTR mutation described herein (optionally, in combination with one or more capsid or additional envelope mutations, as described herein). In other examples, the membrane and envelope proteins are from another flavivirus, such as a Japanese encephalitis virus (e.g., SA14-14-2), a dengue virus (dengue 1, 2, 3, or 4 virus), or another flavivirus described herein.

As with the yellow fever virus vaccine, described above, the 3'UTR mutation(s) can optionally be included in chimeric flaviviruses with one or more additional attenuating mutations, such as an attenuating mutation in the hinge region of the envelope protein of the virus (e.g., a substitution of any one or more amino acids corresponding to yellow fever virus amino acids 48-61, 127-131, and 196-283, e.g., amino acid 279, or one or more of the amino acids in the envelope protein corresponding to amino acids 204, 252, 253, 257, 258, and 261 of dengue 1 virus (see, e.g., WO 03/103571)), an amino acid in the membrane protein (for example, the membrane helix portion of the membrane protein, e.g., an amino acid corresponding to position 66 of the West Nile virus membrane protein), or any of the capsid or envelope protein mutations described herein (e.g., amino acid substitutions at positions corresponding to West Nile virus amino acids 138, 176, 177, 244, 264, and 280, alone or in combination). Specific examples of highly attenuated viruses containing combinations of different types of attenuating mutations are described below. These represent chimeric yellow fever-West Nile variants in which the C2 deletion in the capsid protein is combined with the d7, dB, or dD deletions in the 3'UTR, or with the E#5 combination of amino acid changes in the envelope protein (E176, E177, and E280 amino acid changes).

Capsid Mutations

As is discussed further below, we found that short deletion mutations within the capsid protein could also be used to provide further attenuation for an already attenuated vaccine candidate. Thus, the invention includes flaviviruses (including chimeric flaviviruses, such as vaccine candidates already including other attenuating mutations) that include short deletions (e.g., deletions of 1, 2, 3, or 4 amino acids) in the capsid protein. Examples of such mutations, provided in reference to the YF17D virus capsid protein, include viable deletions affecting Helix I of the protein (see FIG. 2A). A specific example of such a mutation is mutation C2, which includes a deletion of amino acids PSR from Helix I (FIG. 2A). Other short mutations in this region can be tested for viability and attenuation, and are also included in the invention. Capsid protein sequences of other flaviviruses have been published, e.g., for TBE, WN, Kunjin, JE, and dengue viruses (e.g., Pletnev et al., Virology 174:250-263, 1990).

As with the 3'UTR mutations discussed above, the capsid protein mutations can be introduced into a yellow fever virus vaccine strain (e.g., YF17D), optionally in combination with any one or more of the following mutations: 3'UTR mutations as described herein (e.g., d7, dB, dC, dD, or a variant thereof); attenuating mutations in the hinge region of the envelope protein of the virus (e.g., a substitution of any one or more of envelope amino acids 48-61, 127-131, and 196-283, e.g., amino acid 279, or one or more of the amino acids in yellow fever virus corresponding to amino acids 204, 252, 253, 257, 258, and 261 of dengue 1 virus (see, e.g., WO 03/103571)), an amino acid in the membrane protein of yellow fever virus (for example, the membrane helix portion of the membrane protein, e.g., an amino acid corresponding to position 66 of the West Nile virus membrane protein), or any of the envelope protein mutations described herein (e.g., amino acid substitutions at positions corresponding to West Nile virus positions 138, 176, 177, 244, 264, and 280, alone or in combination).

Similarly, the capsid protein mutations can be introduced into chimeric flaviviruses. In one example, which is described further below, one or more of the capsid mutations described herein is included in a vaccine candidate (referred to herein as ChimeriVax™-WN02) that includes capsid and non-structural proteins of yellow fever virus (YF17D) and membrane and envelope proteins of West Nile virus (NY99), the envelope protein of which already includes attenuating mutations (substitutions at positions 107, 316, and 440; WO 2004/045529; also see below). Thus, the invention includes ChimeriVax™-WN-02 that also includes, for example, the C2 mutation (optionally, in combination with one or more 3'UTR and/or additional envelope mutations, as described herein, e.g., the constructed and characterized combinations of the C2 deletion with the d7, dB, or dD deletions in the 3'UTR, or with the E#5 combination of amino acid changes in the envelope protein). In other examples, the membrane and envelope proteins are from another flavivirus, such as a Japanese encephalitis virus (e.g., SA14-14-2), a dengue virus (dengue 1, 2, 3, or 4 virus), or another flavivirus described herein. In other examples, such mutations are introduced into natural (non-chimeric) flaviviruses, as discussed above.

Further, the 3'UTR mutation(s) can optionally be included in chimeric flaviviruses with one or more additional attenuating mutations, such as an attenuating mutation in the hinge region of the envelope protein of the virus (e.g., a substitution of any one or more amino acids corresponding to yellow fever virus envelope amino acids 48-61, 127-131, and 196-283, e.g., amino acid 279, or one or more of the amino acids in the envelope protein corresponding to amino acids 204, 252, 253, 257, 258, and 261 of dengue 1 virus (see, e.g., WO 03/103571)), an amino acid in the membrane protein (for example, the membrane helix portion of the membrane protein, e.g., an amino acid corresponding to position 66 of the West Nile virus membrane protein), or any of the envelope protein mutations described herein (e.g., amino acid substitutions at positions corresponding to West Nile virus amino acids 138, 176, 177, 244, 264, 280, 313, 316, 380, and 440, alone or in combination).

Envelope Mutations

As discussed elsewhere herein, certain envelope mutations have been described as being attenuating for flaviviruses, such as yellow fever virus (e.g., YF17D) and chimeric flaviviruses. These include hinge region mutations (e.g., substitutions at positions corresponding to amino acids 48-61, 127-131, 170, 173, 200, 299, 305, 380, and 196-283 of yellow fever virus and substitutions in residues lining the hydrophobic pocket of the domain II (Hurrelbrink et al., Adv. Virus Res. 60:1-42, 2003; Modis et al., Proc. Natl. Acad. Sci. U.S.A. 100:6986-6991, 2003; see FIG. 3) including residues 52 and 200 in the case of yellow fever virus (FIG. 3), amino acid 279 of Japanese encephalitis virus (in the context of a yellow fever-based chimera), and amino acids 204, 252, 253, 257, 258, and 261 of dengue 1 virus (see, e.g., WO 03/103571)), as well as substitutions in amino acids 107, 316, and 440 of the West Nile virus envelope protein (see, e.g., WO 2004/045529).

As discussed further below, in the examples, we have discovered that mutations (e.g., substitutions) in flavivirus envelope sequences can also provide a means for fine-tuning the attenuation of an already attenuated flavivirus. Thus, the invention includes flaviviruses (e.g., yellow fever virus or a chimeric flavivirus, as described herein) that include one or more envelope protein mutations that can be used to fine-tune the attenuation of a candidate vaccine. Examples of such mutations include substitutions in positions corresponding to amino acids 138, 176, 177, 244, 264, and 280 of West Nile virus, and combinations of these mutations (e.g., 176, 177, and 280; 176, 177, 244, 264, and 280; and 138, 176, 177, and 280). Envelope mutations such as these, which provide a small decrease in attenuation of an already attenuated vaccine candidate, can be included in equivalent positions in a yellow fever virus vaccine (e.g., a YF17D-based vaccine) or a chimeric flavivirus, as described herein. Optionally, these mutations can be included with one or more of the other envelope, capsid, membrane, and/or 3'UTR mutations described herein.

All mutations described for the capsid genes and the 3'UTR's can be combined with these envelope mutations (with one envelope residue or multiple residues shown to affect attenuation) to produce a virus with an attenuated phenotype that is less viscerotropic (i.e., induces lower viremia in the host) than each of the non-combined parent viruses. For example, C2 mutant (Table 2) can be combined with E#7 (Table 4) or dC, dD, etc. 3'UTR deletions (Table 1) can be combined with C2 or E#7 viruses.

Mutations that can be Included with 3'UTR, Capsid Protein, and Envelope Protein Mutations of the Invention In addition to one or more of the attenuating mutations noted above, the flaviviruses of the invention can include other attenuating mutations. Although mentioned above with respect to combinations with each of the three types of mutations included in the invention, this section provides a more detailed description of these mutations.

Examples of mutations that can be included in flaviviruses (including chimeric flaviviruses) that include the mutations of the invention include mutations in the hinge region of the envelope protein or certain membrane protein mutations. In particular, it has been found that certain envelope protein hinge region mutations reduce viscerotropism. The polypeptide chain of the envelope protein folds into three distinct domains: a central domain (domain I), a dimerization domain (domain II), and an immunoglobulin-like module domain (domain III). The hinge region is present between domains I and II and, upon exposure to acidic pH, undergoes a conformational change (hence the designation "hinge") that results in the formation of envelope protein trimers that are involved in the fusion of viral and endosomal membranes, after virus uptake by receptor-mediated endocytosis. Prior to the conformational change, the proteins are present in the form of dimers.

Numerous envelope amino acids are present in the hinge region including, for example, amino acids 48-61, 127-131, and 196-283 of yellow fever virus (Hurrelbrink et al., Adv. Virus Res. 60:1-42, 2003; Rey et al., Nature 375:291-298, 1995). Attenuating mutations in any of these amino acids, or closely surrounding amino acids (and corresponding amino acids in other flavivirus envelope proteins), can be present in the viruses of the invention. Of particular interest are amino acids within the hydrophobic pocket of the hinge region (Modis et al., Published online before print May 20, 2003, 10.1073/pnas.0832193100. PNAS|Jun. 10, 2003|vol. 100|no. 12|6986-6991). As a specific example, a substitution of envelope protein amino acid 204 (K to R in dengue 1 virus), which is in the hydrophobic pocket of the hinge region, in a chimeric flavivirus including dengue 1 sequences inserted into a yellow fever virus vector results in attenuation. This substitution leads to an alteration in the structure of the envelope protein, such that intermolecular hydrogen bonding between one envelope monomer and another in the wild type protein is disrupted and replaced with new intramolecular interactions within monomers. Thus, additional substitutions can be used to increase intramolecular interactions in the hydrophobic pocket, leading to attenuation. Examples of such mutations/substitutions that can be made in the hydrophobic pocket, in combination with the mutations of the invention, include substitutions in E202K, E204K, E252V, E253L, E257E, E258G, and E261H.

In addition to the 3'UTR, capsid, and/or envelope mutations noted above, the flaviviruses of the invention can also include one or more attenuating mutations in the membrane protein, e.g., in an amino acid corresponding to amino acid 66 of the membrane protein of West Nile virus and/or in other amino acids within the predicted membrane helix (e.g., in any one or more amino acids corresponding to amino acids 40-75 of West Nile virus). As a specific example, in the case of a West Nile virus membrane protein, the membrane protein amino acid 66 (leucine in wild type West Nile virus) can be replaced with another amino acid, such as proline. In addition to proline, other hydrophobic amino acids, such as isoleucine, methionine, or valine, or small amino acids, such as alanine or glycine, can substitute the wild type amino acid at position 66 of the membrane protein. As other examples, amino acids at positions 60, 61, 62, 63, and/or 64 of West Nile virus (or corresponding positions in other flaviviruses) can be substituted, alone or in combination with each other, a mutation at position 66, and/or another mutation(s). Examples of substitutions at these positions include: arginine to glycine at position 60, valine to alanine at position 61, valine to glutamic acid or methionine at position 62, phenylalanine to serine at position 63, and valine to isoleucine at position 64. Another example includes an arginine to cysteine mutation at position 60 of JE-specific membrane protein in ChimeriVax™-JE virus, which was found to increase genetic stability of the vaccine during large-scale manufacturing. We also provided, for the first time, evidence that the ectodomain of the M protein is of important functional significance, because a glutamine to proline change at the M5 residue of ChimeriVax™-JE increased the pH threshold of infection (see application PCT/US2005/037369).

In addition to one or more of the membrane protein mutations noted above, the viruses of the invention can also include one or more additional mutations. For example, in the case of West Nile virus, such an additional mutation(s) can be in the region of position 107 (e.g., L to F), 316 (e.g., A to V), or 440 (e.g., K to R) (or a combination thereof) of the West Nile virus envelope protein. The mutations can thus be, for example, in one or more of amino acids 102-112, 138 (e.g., E to K), 176 (e.g., Y to V), 177 (e.g., T to A), 244 (e.g., E to G), 264 (e.g., Q to H), 280 (e.g., K to M), 311-321, and/or 435-445 of the West Nile envelope protein. As a specific example, using the sequence of West Nile virus strain NY99-flamingo 382-99 (GenBank Accession Number AF196835) as a reference, lysine at position 107 can be replaced with phenylalanine, alanine at position 316 can be replaced with valine, and/or lysine at position 440 can be replaced with arginine. Corresponding mutations can be made in other flaviviruses as well.

Further, the viruses of the invention can also include any other mutations that may or may not be attenuating, but are otherwise beneficial for the vaccine (e.g., for vaccine manufacturing), for example, nucleotide changes in the UTRs or amino acid changes in structure or nonstructural proteins that can spontaneously accumulate during virus propagation and be desirable. For instance, we recently observed an R to C amino acid change at residue 60 accumulating in ChimeriVax™-JE vaccine during large scale manufacturing in serum-free conditions. This change did not affect immunogenicity or attenuation, but it stabilized the virus by increasing its growth rate and preventing accumulation of an undesirable reversion to a wild type residue in the envelope protein (E107).

Mutations can be made in the viruses of the invention using standard methods, such as site-directed mutagenesis. The mutations described above are deletions and substitutions, but other types of mutations, such as insertions, can be used in the invention as well. In addition, as is noted above, the mutations can be present singly or in the context of one or more additional mutations. Further, in addition to the specific amino acids noted above, the substitutions can be made with other amino acids, such as amino acids that would result in a conservative change from those noted above. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine. Further, both conservative and non-conservative changes can be selected for analysis of their attenuating effect(s) based on computer-predicted (using protein structure modeling software) changes they cause in the E protein X-ray structure.

The viruses (including chimeras) of the present invention can be made using standard methods in the art. For example, an RNA molecule corresponding to the genome of a virus can be introduced into primary cells, chick embryos, or diploid cell lines, from which (or the supernatants of which) progeny virus can then be purified. Another method that can be used to produce the viruses employs heteroploid cells, such as Vero cells (Yasumura et al., Nihon Rinsho 21, 1201-1215, 1963). In this method, a nucleic acid molecule (e.g., an RNA molecule) corresponding to the genome of a virus is introduced into the heteroploid cells, virus is harvested from the medium in which the cells have been cultured, harvested virus is treated with a nuclease (e.g., an endonuclease that degrades both DNA and RNA, such as Benzonase™; U.S. Pat. No. 5,173,418), the nuclease-treated virus is concentrated (e.g., by use of ultrafiltration using a filter having a molecular weight cut-off of, e.g., 500 kDa), and the concentrated virus is formulated for the purposes of vaccination. Details of this method are provided in WO 03/060088 A2, which is incorporated herein by reference.

The viruses of the invention can be administered as primary prophylactic agents in those at risk of infection, or can be used as secondary agents for treating infected patients. Because the viruses are attenuated, they are particularly well suited for administration to "at risk individuals" such as the elderly, children, or HIV infected persons. The vaccines can also be used in veterinary contexts, e.g., in the vaccination of horses against West Nile virus infection, or in the vaccination of birds (e.g., valuable, endangered, or domestic birds, such as flamingos, bald eagles, and geese, respectively). Further, the vaccines of the invention can include a virus, such as a chimeric virus, including a particular mutation, in a mixture with viruses lacking such mutations.

Formulation of the viruses of the invention can be carried out using methods that are standard in the art. Numerous pharmaceutically acceptable solutions for use in vaccine preparation are well known and can readily be adapted for use in the present invention by those of skill in this art (see, e.g., *Remington's Pharmaceutical Sciences* ($18^{th}$ edition), ed. A. Gennaro, 1990, Mack Publishing Co., Easton, Pa.). In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the yellow fever 17D vaccine, e.g., as a clarified suspension of infected chicken embryo tissue, or a fluid harvested from cell cultures infected with a chimeric virus.

The vaccines of the invention can be administered using methods that are well known in the art, and appropriate amounts of the vaccines to be administered can readily be determined by those of skill in the art. What is determined to be an appropriate amount of virus to administer can be determined by consideration of factors such as, e.g., the size and general health of the subject to whom the virus is to be administered. For example, the viruses of the invention can be formulated as sterile aqueous solutions containing between $10^2$ and $10^8$, e.g., $10^3$ to $10^7$, infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177-203), the viruses can be administered by mucosal routes as well. Further, the vaccines of the invention can be administered in a single dose or, optionally, administration can involve the use of a priming dose followed by a booster dose that is administered, e.g., 2-6 months later, as determined to be appropriate by those of skill in the art.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, polyphosphazine, CpG oligonucleotides, or other molecules that appear to work by activating Toll-like Receptor (TLR) molecules on the surface of cells or on nuclear membranes within cells. Although these adjuvants are typically used to enhance immune responses to inactivated vaccines, they can also be used with live vaccines. Both agonists of TLRs or antagonists may be useful in the case of live vaccines. In the case of a virus delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

In the case of dengue viruses and/or chimeric flaviviruses including membrane and envelope proteins of a dengue virus, against which optimal vaccination can involve the induction of immunity against all four of the dengue serotypes, the viruses of the invention can be used in the formulation of tetravalent vaccines. Any or all of the viruses used in such tetravalent formulations can include one or more mutations that decrease viscerotropism, as is described herein. The viruses can be mixed to form tetravalent preparations at any point during formulation, or can be administered in series. In the case of a tetravalent vaccine, equivalent amounts of each virus may be used. Alternatively, the amounts of each of the different viruses present in the administered vaccines can vary (WO 03/101397 A2).

The flaviviruses of the invention can also be used to deliver heterologous gene products, such as vaccine antigens or other therapeutic agents (see, e.g., WO 02/102828; U.S. Pat. No. 6,589,531; and WO 02/072835).

The invention is based, in part, on the following experimental results.

Experimental Results and Examples

Background and Summary

In one example of the invention, mutations such as those described above were made in a chimeric flavivirus vaccine candidate, referred to herein as ChimeriVax™-WN02, which comprises the capsid and non-structural proteins of a yellow fever virus (YF17D) and the premembrane and envelope proteins of a West Nile virus (NY99) as is described further below. This vaccine candidate has been tested in preclinical and Phase I clinical studies. Although it appeared highly attenuated and immunogenic in mice and rhesus monkeys, it induced a more active replication in cynomolgus monkeys and in several human volunteers in Phase I trials (N=45) compared to a control yellow fever (YF) 17D vaccine as judged by post-inoculation viremia. Even though it was well tolerated in the Phase I trial and highly immunogenic, based on the viremia levels, we undertook studies to improve further the safety profile of ChimeriVax™-WN02 by means of specific mutagenesis, with a goal of obtaining a slight decrease in viremia in small animals (hamsters) compared to the ChimeriVax™-WN02 variant. Three mutagenesis approaches were employed, and are each discussed in the examples set forth below. In a first approach, small nucleotide deletions were introduced into the 3'-untranslated region of the virus (the 3'UTR). In a second approach, amino acid deletions were introduced into the capsid protein. In a third approach, specific attenuating amino acid substitutions were introduced into the envelope protein of the virus. As is discussed further below and elsewhere herein, these types of mutations can be combined with each other (and other attenuating or otherwise beneficial mutations) to make viruses of the invention.

ChimeriVax™-WN02

An initial YF17D/WN chimera containing the wild type prM-E gene sequence from the NY99 strain of WN virus, designated ChimeriVax™-WN01, was constructed using a standard two-plasmid system (Arroyo et al., J. Virol. 78:12497-12507, 2004). The JE-specific prM-E gene sequences in plasmids pYF5'3'IV/SA14-14-2 (contains 5' and 3' portions of cDNA for ChimeriVax™-JE vaccine virus) and pYFM5.2/SA14-14-2 (contains a large intermediate portion of ChimeriVax™-JE cDNA) were replaced with the corresponding cDNA sequences of the NY99 WN parent. ChimeriVax™-WN01 virus was obtained by in vitro ligation of fragments from the resulting pYWN5'3'N1Δ3 and pYWN5.2/5 plasmids to obtain full-length DNA template, followed by in vitro transcription and transfection of Vero cells by the resulting RNA transcripts. The new chimeric virus was shown to be significantly attenuated for mice and rhesus monkeys as compared to WN NY99 and YF17D, although it retained a slight degree of neurovirulence for adult mice. It was further attenuated by the introduction of three SA14-14-2 JE vaccine-specific amino acid changes at residues E107, E316, and E440 (see Table 3 below) of the envelope (E) protein. The two new plasmids containing these mutations were designated pYWN5'3'NF3Δ2 and pYWN5.2 316/440#2. Based on the results of testing the resulting triple-mutant, designated ChimeriVax™-WN02, in mice and monkeys, it was concluded that it was sufficiently attenuated to be further tested in Phase I clinical trials. The trials were performed in healthy adults (N=30 for inoculation dose of 5 $\log_{10}$ pfu and N=15 for 3 $\log_{10}$ pfu dose). Unexpectedly, several of the inoculated volunteers in both dose groups developed viremia that was statistically significantly higher (up to 3.5 times) compared to YF-Vax control. This indicated that, although the vaccine was well tolerated and immunogenic, further development could be done to obtain a more attenuated ChimeriVax™-WN vaccine variant. High viremia levels can be indicative of excessive virus replication in peripheral organs, and may present a risk of developing hemorrhagic symptoms in a subset of vaccinees, similar to classical yellow fever, or encephalitis due to crossing the blood-brain barrier, which can be facilitated by high viremia based on knowledge for encephalitogenic flaviviruses.

Thus, the only suboptimal parameter of the ChimeriVax™-WN02 vaccine was a slightly higher than expected post-inoculation viremia observed in a proportion of human volunteers, which may be indicative of an excessive replication in peripheral organs (viscerotropism). Since the starting ChimeriVax™-WN02 virus is already a highly attenuated vaccine candidate, rather than a virulent wild type isolate, we sought to identify new mutation(s) that did not overattenuate the vaccine. We sought mutations that prevented the occurrence of high viremia in an appropriate animal model(s) (in the experiment described below we used hamsters) and subsequently in humans, but without significantly reducing efficacy.

The experimental steps involved in the production and characterization of new ChimeriVax™-WN04 candidates included:

Construction of plasmid DNAs containing the desired mutations. Specifically, all mutations were introduced into the initial ChimeriVax™-WN02 plasmids pYWN5'3'NF3Δ2 and pYWN5.2 316/440#2 by standard oligonucleotide-directed mutagenesis using simple or overlap PCR techniques, followed by ligation of the resulting PCR products into these plasmids and selection of mutant plasmids by cloning in E. coli and sequencing of individual clones.

Ligation in vitro of large EagI-BspEI fragments of appropriate plasmids of the pYWN5'3' and pYWN5.2 series to obtain full-length cDNA templates, followed by XhoI linearization.

In vitro transcription of full-length DNA templates with SP6 RNA polymerase to produce synthetic infectious RNA.

Production of mutant ChimeriVax™-WN04 viruses by transfection of Vero cells using lipofectamine or electroporation and harvesting passage 1 (P1) virus samples, followed by an additional passage in serum-free medium to obtain P2 virus stocks.

Confirmation of mutant virus viability by monitoring cytopathic effect (CPE), plaque assay of cell supernatants, and detection of viral RNA by a sensitive RT-PCR.

Confirmation of the presence of desired mutations by consensus sequencing of viral genomic RNA at P2 level (and preliminary analysis of genetic stability by sequencing viruses passaged to P5 level).

Analysis of plaque-morphology and growth properties by standard titration of P2 viruses in Vero cells.

Analysis of viscerotropism in Syrian hamsters inoculated with 5 $\log_{10}$ pfu/dose of P2 virus samples by measuring post-inoculation viremia on days 1-9; analysis of immunogenicity by measuring serum titers of WN virus-specific neutralizing antibodies on day 30 using standard 50% plaque reduction neutralization test ($PRNT_{50}$).

As described below, we introduced deletions into the 3'UTR or the capsid (C) protein of ChimeriVax™-WN02 virus, in an effort to achieve a very slight attenuating effect in this proven, highly attenuated vaccine candidate. This was attained by small deletions, 5-16 nucleotides long, in the 3' UTR, or 3 amino acid deletions in protein C. Some of the deletions in the 3'UTR were short (5-6 nucleotides) deletions that were designed based on a predicted secondary structure of the 3'UTR of YF17D virus (Proutski et al., J. Gen. Virol. 78:1543-1549, 1999). These were aimed to specifically destabilize some of the specific computer-predicted stem-loop structures in the middle of the 3'UTR located outside of any conserved sequence elements. In a third approach, we introduced additional SA14-14-2 attenuating mutations into the E protein of ChimeriVax™-WN02, which was the same method we used to develop ChimeriVax™-WN02 from ChimeriVax™-WN01. Effects of these modifications were monitored in a hamster model. ChimeriVax™-WN04 variants were identified that result in a desired small reduction in viscerotropism in hamsters.

Construction of ChimeriVax™-WN04-3'UTR Candidates by Introducing Specific Deletions in the 3'UTR As discussed above, the organization of the YF17D-specific 3'UTR shared by all ChimeriVax™ viruses is shown in FIG. 1A. It contains in order from the 3' end (i) a conserved for all flaviviruses 3'-extreme stem-and-loop structure, (ii) two conserved sequence elements CS1 and CS2, and (iii) three copies of a repeat sequence element (RS) located in the upstream portion of the 3'UTR (Chambers et al., Annu. Rev. Microbiol. 44:649-688, 1990). One valuable feature of deletions in this region is their stability, as spontaneous reversion during virus replication is virtually impossible. The 11 deletions we introduced into ChimeriVax™-WN02 virus (using plasmid pYWN5'3'NF3Δ2) to generate new ChimeriVax™-WN04-3'UTR candidates are shown in FIG. 1A and include:

a dRS deletion removing the three RS elements (nucleotides 18-164, ATAACCGGG (SEQ ID NO:27) . . . - . . . TCCACAC (SEQ ID NO: 28), of the YF17D 3' UTR; numbering is from the first 3'UTR nucleotide after the TGA termination codon of the viral ORF);

four small, 5-6 nucleotide deletions: dA (nucleotides 229-234, GCAGTG; SEQ ID NO: 29), dB (nucleotides 256-260, CAGGT; SEQ ID NO: 30), dC (nucleotides 293-297, CCAGA; SEQ ID NO: 31), and dD (nucleotides 308-312, CGGAG; SEQ ID NO: 32) occurring between the RSs and CS2, designed to destabilize individual computer predicted stem-loop/pseudoknot structures (Proutski et al., J. Gen. Virol. 78:1543-1549, 1999) shown in FIG. 2B;

a large, 105 nucleotide deletion, d105 (nucleotides 218-321, TAAGCT (SEQ ID NO: 33) . . . - . . . CCGCTA (SEQ ID NO: 34)), which removes most of the nucleotides between the RSs and CS2 (a similar deletion was tolerated by wild type DEN4 but significantly reduced replication in vitro and in vivo (Men et al., J. Virol. 70:3930-3937, 1996) and therefore we expected that it could be overattenuating for ChimeriVax™-WN02);

a 30 nucleotide deletion, d30 (nucleotides 322-351, CCACCC (SEQ ID NO: 35) . . . - . . . GACGG (SEQ ID NO: 36)), upstream from the CS2, mimicking the MO mutation originally described to attenuate wild type DEN4 virus (Men et al., J. Virol. 70:3930-3937, 1996; U.S. Pat. No. 6,184,024 B1);

two smaller deletions, d7 (nucleotides 345-351, AAGACGG; SEQ ID NO: 25) and d14 (nucleotides 338-351, TGGTAGAAAGACGG; SEQ ID NO: 8), in the MO region, which were tested because we expected that the above-described d30 mutation could over-attenuate ChimeriVax™-WN02 in vitro and/or in vivo;

two small 5 and 16 nucleotide deletions in the CS2 region designated CS2d5 (nucleotides 360-364, GGTTA) and CS2d16 (nucleotides 360-375, GGTTAGAGGAGACCCT; SEQ ID NO: 7).

Viability of mutant viruses was monitored by careful microscopic observation of CPE during P1 and P2 passages, as well as subsequent passages up to P5 done to assess genetic stability of viable mutants and to determine whether any second-site mutations would restore viability of apparently non-viable mutants. These observations were confirmed by RT-PCR and plaque assay in Vero cells. Plaque assay also yielded important information on mutant virus titers indicative of growth properties in Vero cells and on changes in plaque-morphology rendered by introduced deletions. Relevant portions of the genomes of viable viruses were sequenced at P2 and P5 levels. The results of these experiments are summarized in Table 1.

Based on the data in Table 1, we concluded:

1) Despite the large size of the dRS deletion, it rendered no marked attenuation in vitro, because the mutant virus produced large and clear plaques, similar to those of the ChimeriVax™-WN02 LP control (large plaque control; see footnote 1 of Table 1), and grew to a relatively high titer of $6 \times 10^6$ PFU/ml. This result was expected, because a similar deletion had almost no effect on YF17D virus replication in vitro (Bredenbeek et al., J. Gen. Virol. 84:1261-1268, 2003), and a similar large deletion did not reduce neurovirulence of ChimeriVax™-JE virus in suckling mice.

2) The small deletions, dA, dB, dC, and dD, caused marked attenuation in vitro judged by plaque morphology. The plaque sizes of all four mutant viruses were reduced; plaques of the dD virus were opaque (plaques of both LP and SP WN02 controls are clear). The viruses grew to relatively high titers during P2 passage in the excess of 6 $\log_{10}$ PFU/ml, which is a desirable feature for manufacturing (Table 1; except for the dA mutant titer, which could not be determined because it formed too tiny plaques to be counted in this experiment). These results indicated that the predicted stem-loop/pseudoknot structures (FIG. 1B) do exist and are important for flavivirus replication. In contrast to wild type DEN4 virus, which tolerated large deletions in this region upstream from CS2 (Men et al., J. Virol. 70:3930-3937, 1996), the large d105 deletion, encompassing all structural elements targeted by small deletions, was overattenuating (lethal) for ChimeriVax™-WN02 virus.

3) the d30 deletion, which is analogous to the Δ30 mutation (Men et al., J. Virol. 70:3930-3937, 1996; U.S. Pat. No. 6,184,024 B1), as well as a shorter deletion d14, in the region immediately preceding CS2, were lethal. The only mutation in this region that was tolerated by ChimeriVax™-WN02 was the small d7 deletion. It was attenuating as it reduced plaque morphology.

4) The small CS2d5 and CS2d16 deletions had moderate attenuating effects in vitro, as the deletion-containing mutants formed intermediate size, opaque plaques. These mutations were expected to affect the predicted stem-loop structure that includes the sequence of XbaI restriction site at nucleotide 10,708, as shown in FIG. 1B.

In these experiments, we demonstrated for the first time that small deletions outside the conserved elements of the 3'UTR can provide a degree of attenuation. In addition, we demonstrated for the first time that specific destabilization of individual predicted stem-loop/pseudoknot structures results in attenuation. In addition, there are many predicted stem-loop/pseudoknot structures in the 3'UTR of flaviviruses, including YF17D virus, providing a large variety of opportunities to achieve a range of attenuating effects. These structures, or areas between structures, can now be targeted by small deletions that can be introduced by those of skill in the art. Mutagenesis of any of these structures can now be expected, based on our discovery, to provide a degree of attenuation. Choosing from the range of effects allows selection of a mutant with a desired degree of attenuation.

TABLE 1

In vitro characteristics of ChimeriVax ™-WN04-3'UTR deletion mutants

| Mutation | Viability of mutant | P2 titer, PFU/ml | Plaque morphology |
| --- | --- | --- | --- |
| dRS | viable | $6 \times 10^6$ | large, clear |
| dA | viable | N/D[2] | tiny |
| dB | viable | $6.3 \times 10^6$ | smaller than SP control |
| dC | viable | $1.5 \times 10^6$ | tiny |
| dD | viable | $6.6 \times 10^6$ | intermediate, opaque |
| CS2d5 | viable | $1.2 \times 10^7$ | intermediate, opaque |
| CS2d16 | viable | $5.3 \times 10^6$ | intermediate, opaque |
| d7 | viable | $5.2 \times 10^6$ | smaller than SP control |
| d14 | non-viable | N/A | no plaques |
| d30 | non-viable | N/A | no plaques |
| d105 | non-viable | N/A | no plaques |
| WN02 LP control[1] | | | large, clear |
| WN02 SP control[1] | | | small, clear |

[1]The LP and SP control viruses (used for comparison of plaque morphology only in plaque assay) were isolated previously by plaque-purification from a manufacturing ChimeriVax ™-WN02 P5 virus sample which was a population of large plaques (LP) and small plaques (SP); the SP variant appeared due to accumulation of an M66 Leu to Pro amino acid change.
[2]N/D—not determined because plaques were too small when stained with neutral red on day 5 post-infection to be accurately counted.

It should be noted that the true secondary structures of the 3'UTRs of Flaviviruses, including YF 17D virus, are unknown, because there are no available methods to experimentally prove their existence in the context of whole viruses, and therefore published predictions, e.g., the one predicted for YF 17D by Proutski and co-workers (FIG. 1B), may be incorrect. Many alternative structures can be predicted to form in a relatively long RNA molecule (Zuker et al., N. A. R. 19:2707-2714, 2001), and it is possible that different structures (in plus or minus strands) form and function at different steps of the viral life cycle. True structures can be influenced by the formation of various pseudoknots (Olsthoorn et al., RNA 7:1370-1377, 2001) and long-range RNA interactions (e.g., RNA cyclization and other interactions (Alvarez et al., J. Virol. 79:6631-6643, 2005)), as well as possible RNA interactions with host and viral proteins. To further complicate interpretation of published results of theoretical computer predictions, manual operations are often used, such as initial folding of partial sequences with subsequent forcing of initially predicted structures into structures of longer RNA sequences, the artificial use of N's during initial folding steps, and subjective selection of preferred structure elements (e.g., Mutebi et al., J. Virol. 78:9652-9665, 2004). To this end, we folded the 3'UTR RNA sequence of YF 17D using the commonly used Zuker's prediction algorithm. The predicted optimal structure is shown in FIG. 1C, which differs from the Proutsky prediction shown in FIG. 1B. It is important that the small deletions dA, dB, dC, dD, d7, and d14 in FIGS. 1A and 1B generally destabilized the predicted native YF 17D optimal (FIG. 1C) and suboptimal structures. An example of one such altered optimal structure (for the dC mutant) is shown in FIG. 1D. In contrast, the CS2d5 and CS2d16 deletions (FIGS. 1A and 1B) did not noticeably change the optimal native structure, indicating that these deletions may attenuate the virus (attenuation was demonstrated in the hamster model for ChimeriVax™-WN) by virtue of altering the sequence of CS2 per se rather than the 3'UTR structure or, alternatively, by altering some suboptimal structures. Thus, even though some of the deletions were designed based on the Proutski structure prediction (FIG. 1B), their true effect may be due to destabilizing different structure elements than the predicted stem-loops in FIG. 1B.

After the dC mutant was passaged from P2 to P5 passage level in serum-free Vero cells to analyze genetic stability, and the P5 virus was sequenced, it was found that the five-nucleotide deletion spontaneously increased in length to 24 nucleotides (nucleotides 277-300, TCTGGGACCTCCCAC-CCCA deleted; SEQ ID NO: 9). (Other deletions (dRS, d7, CS2d5, CS2d16, dA, dB, and dD) were stable during the same genetic stability passages.) The effect of the increased deletion size was that the predicted secondary structure became similar to the original optimal YF 17D structure (FIG. 1E; compare with FIG. 1C). This spontaneous change appeared to be a cell culture adaptation. Both the P2 and P5 variants were highly attenuated and immunogenic in hamsters (see footnote 4 to Table 5). Thus, the P5 variant of dC mutant may have desired vaccine phenotype.

Construction of ChimeriVax™-WN04-C Candidates by Introducing Specific Deletions in the YF17D-Specific Capsid Protein C Our computer analysis of the YF17D C protein structure using ProteinPredict and Protean methods predicted that its general organization does not differ substantially from that of TBE (FIG. 2B). We reasoned that large deletions in the protein in ChimeriVax™-WN02 would be most likely overattenuating. Therefore, we introduced five small deletions of 3-4 amino acids as shown in FIG. 2B (deleted residues are boxed). Deletions were engineered into the ChimeriVax™-WN02 plasmid pYWN5'3'NF3Δ2, which encompasses the entire C protein gene. The first three deletions (C1-3; each 3 amino acids long) are in the same general area described for TBE in by Kofler et al., J. Virol. 76:3534-3543, 2002. However, we positioned the mutations so as to allow for testing of the importance of specific structural features: the C1 deletion is located upstream from both the central hydrophobic stretch and the predicted Helix I, C2 affects Helix I only, and C3 was expected to interfere with both Helix I and the central hydrophobic stretch. Additionally, the C4 deletion (4 amino acids in length) was designed to target the predicted Helix III in the carboxy-terminal, positively charged portion of the protein, and the C5 deletion (3 amino acids) is between Helices III and IV (it also eliminates the NS2b/NS3-viral protease cleavage site at the C terminus of intracellular form of the protein; it was introduced to determine whether any second-site mutations could compensate for the expected defect in processing of the polyprotein).

The results of in vitro characterization of the WN04-C mutants are summarized in Table 2. Only the C1 and C2 mutants were viable, while the C3-C5 deletions were lethal. While the strong deleterious effect of the C5 mutation was not surprising, it was interesting that a small deletion in the carboxy-terminal, positively charged portion of the protein (C4) was lethal, suggesting that sequence/structure alterations in this region cannot be tolerated by the virus. The most surprising observation was that the C3 deletion was also lethal, because it is in the same general area that tolerated large deletions in the context of TBE virus. The presence of deletions in C1 and C2 variants was confirmed by sequencing. The results of sequencing the entire structural protein region in viruses at P2 and P5 levels are shown in Table 2. While the C1 variant accumulated changes at residues M14 and E313, which appeared as heterogeneities at P5 passage, but not P2 (the change at E313 is believed to be an adaptation to serum-free virus growth conditions seen previously accumulating in ChimeriVax™-WN02), the C2 variant appeared to be genetically stable. The latter virus contained a heterogeneity at residue M71 at both P2 and P5, but the ratio of mutant to non-mutant HO %) did not change during passage. Judged by plaque morphology, the C1 variant was not attenuated compared to ChimeriVax™-WN02, while the C2 variant appeared attenuated, because it formed small plaques, suggesting the importance of Helix I. Both mutants grew to high titers in Vero cells (~7 $\log_{10}$ PFU/ml). There is no prior published data indicating that such small deletions can attenuate a flavivirus or have a practical value. Successful generation of viable C1 and C2 mutants in our study provided evidence that YF 17D virus or ChimeriVax™ vaccine viruses can tolerate small deletions upstream from the central hydrophobic region and in the beginning of α-Helix I.

TABLE 2

In vitro characteristics of ChimeriVax ™-WN04-C mutants

| Mutation | Viability of mutant | P2 titer, PFU/ml | Plaque morphology | Sequence at P2[2] | Sequence at P5[2] |
|---|---|---|---|---|---|
| C1 | viable | 1.9 × 10[7] | large, clear | deletion OK; no other mutations | deletion OK; 20% M14 N to H, 40% E313 G to R |

TABLE 2-continued

In vitro characteristics of ChimeriVax™-WN04-C mutants

| Mutation | Viability of mutant | P2 titer, PFU/ml | Plaque morphology | Sequence at P2[2] | Sequence at P5[2] |
|---|---|---|---|---|---|
| C2 | viable | 1.5 × 10[7] | small | deletion OK; 80% M71 A to T | deletion OK; 80% M71 A to T |
| C3 | non-viable | N/A | no plaques | no RT-PCR product | no RT-PCR product |
| C4 | non-viable | N/A | no plaques | no RT-PCR product | no RT-PCR product |
| C5 | non-viable | N/A | no plaques | no RT-PCR product | no RT-PCR product |
| WN02 control[1] | | | large, clear | | |

[1]The WN02 control virus (used for comparison of plaque morphology only in plaque assay) was a P1 sample obtained by transfection of cells with ChimeriVax ™-WN02 in vitro RNA transcripts.
[2]The entire structural protein region (C-prM-E genes) was sequenced by consensus method to confirm the intended deletion and to check for the presence of any other amino acid changes/heterogeneities.

Construction of ChimeriVax™-WN04-E Candidates by Introducing Additional SA14-14-2-Specific Changes in the Envelope (E) Protein The E protein residues that differ in wild type JE virus (Nakayama) and the SA14-14-2 vaccine strain, as well as residues at corresponding positions in WN NY99, are shown in Table 3. As discussed above, a desired degree of attenuation of the ChimeriVax™-WN02 vaccine variant was initially attained by introduction of three SA14-14-2 specific residues, E107, E316, and E440, into the originally constructed YF17D/WN chimera that contained the wild type NY99 strain-specific prM-E genes (the WN01 virus). ChimeriVax™-WN02 (and WN01) also contains the E227 Ser residue coinciding in both SA14-14-2 and NY99 viruses.

TABLE 3

The SA14-14-2 JE vaccine-specific residues in the envelope protein E to be combined in ChimeriVax ™-WN04 to reduce viscerotropism of ChimeriVax ™-WN02[1]

| Amino Acid[2] | Wild-type JE (Nakayama) | JE Vaccine SA14-14-2 | Wild-type WN (NY99) |
|---|---|---|---|
| 107 | L | F | L |
| 138 | E | K | E |
| 176 | I | V | Y |
| 177 | T | A | T |
| 227 | P | S | S |
| 244 | E | G | E |
| 264 | Q | H | Q |
| 280 | K | M | K |
| 316 | A | V | A |
| 440 | K | R | K |

[1]SA-14-14-2 specific residues already present in ChimeriVax ™-WN02 are in bold; note that residue E227 is the same (Ser) in SA14-14-2 and WN NY99 and therefore did not require changing by specific mutagenesis.
[2]Amino acid numbers are according to numbering in WN virus E protein.

Figure 4:
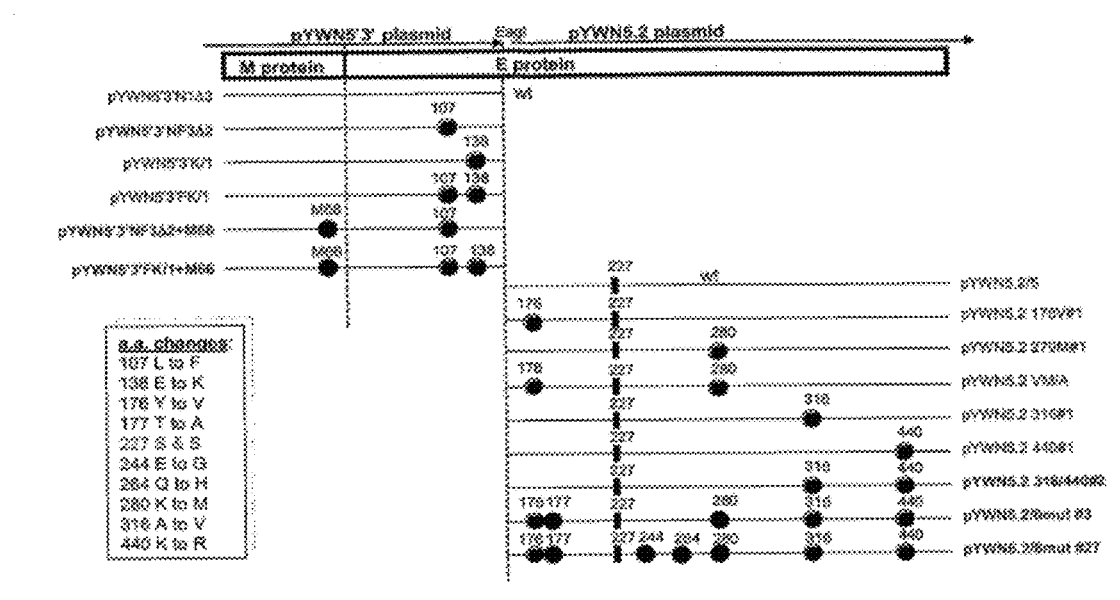

All plasmids constructed previously in the process of selection of the WN02 vaccine candidate (Arroyo et al., J. Virol. 78:12497-12507, 2004) and those we constructed more recently (two bottom pYWN5'3' and pYWN5.2 constructs) are depicted in FIG. 4. Desired sets of SA14-14-2 mutations in the E protein of chimeric virus were obtained by in vitro ligation of specific pairs of DNA fragments from appropriate pYWN5'3' and pYWN5.2 plasmids via the EagI restriction site in the E gene, e.g., ChimeriVax™-WN02 was generated by ligation of pYWN5'3'NF3Δ2 and pYWN5.2 316/440#2. Some of the combinations have been tested previously in mice and monkeys, leading to the selection of the WN02 candidate for further testing in humans (Arroyo et al., J. Virol. 78:12497-12507, 2004). The M66 mutation (Leu to Pro change at residue 66 of M protein) that we incorporated into the two new pYWN5'3' plasmids was a cell culture adaptation that accumulated in the ChimeriVax™-WN02 vaccine during large-scale manufacturing. It reduced plaque size of the virus, but had no effect on mouse neurovirulence (Arroyo et al., J. Virol. 78:12497-12507, 2004). According to our recent results from Phase I human trials and additional monkey experiments, it decreased viscerotropism of the virus for primates and thus appears to be a beneficial mutation for vaccine performance, increasing safety. Because the current ChimeriVax™-WN02 vaccine is a mixture of large and small plaques, inducing slightly higher than expected viremia in some humans, additional work was done to decrease viscerotropism. For instance, the small plaque variant was recently plaque purified and is being currently tested in monkeys. Newly constructed variants with previously untested combinations of mutations are described below.

TABLE 4

New ChimeriVax ™-WN04-E variants: introduced mutations and in vitro characterization of viruses

| Virus[1] | Intended mutations[2] | P2 Titer | Apparent plaque morphology[3] | Sequence at P2[4] | Sequence at P5[4] |
|---|---|---|---|---|---|
| 3 | WN02 + E138 | 6.1 × 10[6] | <L + S | OK, but possible E166 R/L | 95% E166 R to L, 80% E313, E138 K/T |

TABLE 4-continued

New ChimeriVax ™-WN04-E variants: introduced mutations and in vitro characterization of viruses

| Virus[1] | Intended mutations[2] | P2 Titer | Apparent plaque morphology[3] | Sequence at P2[4] | Sequence at P5[4] |
|---|---|---|---|---|---|
| 4 | WN02 + E138 + M66 | $4.0 \times 10^4$ | TINY | n.d. | n.d. |
| 5 | WN02 + E176, 177, 280 | $6.8 \times 10^7$ | <L + S | OK, but E313 G/R (80% R) | E313, M63 F to S, 50% E167 F to V |
| 5A | WN02 + E176, 177, 280 | $6.75 \times 10^7$ | <L + S | n.d. | n.d. |
| 6R | WN02 + E176, 177, 244, 264, 280 | $2.15 \times 10^7$ | <L + S | no expected E244; E167 F to L, possible E221 L/F, a silent nucleotide change | n.d. |
| 6A | WN02 + E176, 177, 244, 264, 280 | $4.0 \times 10^6$ | <L + S | | E244 V instead of expected G, E313, 50% M67 (L to S), |
| 7 | WN02 + E138, 176, 177, 280 | $1.18 \times 10^7$ | <L + S | OK, but clear E313 G to R | E313, E166 R to Q, possible trace of E138 wt E |
| 7A | WN02 + E138, 176, 177, 280 | $6.95 \times 10^6$ | <L + S | n.d. | n.d. |
| 11 | All ten SA14-14-2 residues | none | none | no RT-PCR product | no RT-PCR product |
| 1R control | WN02 | $2.45 \times 10^7$ | L + S | OK | n.d. |
| 2 control | WN02 + M66 | $2.95 \times 10^6$ | S | OK, but E313 G/R (~20% R) | E313, only 20% M66 (reversion) |

[1]All viruses were obtained by transfection of Vero cells; in virus designations, "A" denotes a variation in preparation of full-length DNA template (3-fragment ligation) and "R" denotes a virus obtained from a repeated transfection; viruses that are shaded were selected for further testing in hamsters.
[2]WN02 SA14-14-2-specific residues: E107, 227, 316, and 440; M66 change is a cell culture adaptation known to reduce plaque size of WN02 virus.
[3]L + S, an apparent mixture of large and small plaques (in 1R virus); S, small plaques; <L + S, plaques appeared to be a mixture of large and small plaques, but overall size was somewhat smaller than for the 1R virus (L + S).
[4]The entire structural protein region (C-prM-E genes) was sequenced by consensus method to confirm intended mutations (each confirmed unless indicated otherwise); other detected amino acid changes/heterogeneities are listed.

The data on viability and in vitro characterization of new ChimeriVax™-WN04-E constructs are summarized in Table 4. Virus 11, in which we attempted to combine all ten SA14-14-2-specific residues, appeared to be non-viable because it did not induce CPE after transfection, during subsequent passages did not form plaques in plaque assay, and its genomic RNA could not be detected in cell supernatants by a sensitive RT-PCR reaction. Other new viruses containing 5 to 9 SA14-14-2 changes listed in Table 4 were viable (all 3, 4, 5, 6, and 7 samples). Most of these appeared slightly attenuated because their plaques were somewhat smaller than plaques of WN02 control (virus 1R), while they grew to relatively high titers in the excess of 6-7 $\log_{10}$ pfu/ml; the only exception was virus 4, which appeared to be over-attenuated (tiny plaques and very low titer) due to the simultaneous addition of E138 and M66 mutations.

The intended SA14-14-2 changes were confirmed by consensus sequencing in viruses 3, 5, and 7. Virus 6 was curious, because its 6R sample lacked one of the intended mutations when sequenced at P2: it had a wild type Glu at residue E244 instead of Gly (it also lacked two silent nucleotide changes intentionally introduced downstream from E244 triplet to create an SphI restriction site). Another sample, 6A, had a Val at residue E244 that differs from both wild type WN and SA14-14-2 sequence (it had the intended SphI site). These changes in viral sequences were unexpected, because the entire virus-specific region in the pYWN5.2/8mut plasmid preparation used to generate 6R, 6A, and 11 in vitro RNA transcripts had been confirmed by sequencing. It is possible that the E244 SA14-14-2-specific change is lethal for Chi-meriVax™-WN, alone or in combination with some other changes such as E264, which would explain why virus 11 could not be recovered. The detected modifications of this residue in 6R and 6A samples that restored viability could be due to a mistake by viral polymerase during virus replication (most likely the case for virus 6A), pYWN5.2/8mut plasmid instability in bacteria, or minor contamination by another bacterial clone not revealed by plasmid sequencing. The sequenced P2 viruses were relatively homogeneous, except that some viruses started showing accumulation of a few additional mutations, some of which could be expected (e.g., the E313 G to R change, which is a known serum-free cell culture adaptation of ChimeriVax™-WN that does not affect biological phenotype). More diverse mutations accumulated during propagation to P5 level. Based on these observations, viruses 3, 5, 6A, and 7 at P2 level (shaded in Table 4) were selected for further testing for viscerotropism/immunogenicity in hamsters.

Analysis of Viscerotropism and Immunogenicity of ChimeriVax™-WN04 Variants in Hamsters Mice are used as a sensitive small animal model to demonstrate reduced neurovirulence, which is an important indicator of attenuation, and high immunogenicity of ChimeriVax™-WN vaccine candidates (Arroyo et al., J. Virol. 78:12497-12507, 2004). However, this model cannot be used to predict the level of viscerotropism in monkeys and humans, which is another important attribute of attenuation, because chimeras do not induce detectable viremia in mice. Some flaviviruses induce high-level viremia in hamsters, as recently shown for wild type WN virus (Tesh et al., Emerg. Inf. Dis.

8:1392-1397, 2002). Our recent studies using the ChimeriVax™-WN02 vaccine (a mixture of large and small plaque viruses) and plaque purified LP and SP variants demonstrated a good correlation between viremia caused by these viruses in female Syrian hamsters and viremia observed in human volunteers and cynomolgus monkeys. Specifically, the LP variant, which is less attenuated for humans, induced a readily detectable viremia in hamsters, while the more attenuated SP virus induced a very low or undetectable viremia. We used this new small animal model to investigate whether the above-described WN04 mutations reduced viscerotropism, without precluding the development of efficient anti-WN immune response.

All procedures were performed in accordance with NIH requirements for humane treatment of laboratory animals under a protocol approved by Acambis IACUC. Four-week old female Syrian hamsters were inoculated sub-cutaneously (SC) with 5 $\log_{10}$ pfu of selected ChimeriVax™-WN04 candidates, as well as WN02 LP and SP control viruses or ~4 $\log_{10}$ pfu of YF17D, followed by measurements of viremia on days 1, 3, 5, 7, and 9 (animals were bled under anesthesia and virus titers in harvested sera were determined by plaque assay) and antibody responses on day 30 measured by standard 50% plaque-reduction neutralization test ($PRNT_{50}$), in individual animals. The results are shown in Table 5.

TABLE 5

Viremia and antibody responses to ChimeriVax ™-WN04 variants following SC inoculation of female Syrian hamsters

| Virus[1] | Hamster No. | Viremia, PFU/ml[2] | | | | | Mean peak viremia titer | Mean viremia duration (days) | $PRNT_{50}$ (day 30)[3] |
|---|---|---|---|---|---|---|---|---|---|
| | | Day 1 | Day 3 | Day 5 | Day 7 | Day 9 | | | |
| ChimeriVax ™-WN04-C1 | 1 | — | 1,750 | 125 | — | — | 1,340 | 3.4 | 2,560 |
| | 2 | 125 | 1,200 | — | — | — | | | >10,240 |
| | 3 | — | 1,300 | 1,250 | — | — | | | 1,280 |
| | 4 | — | 625 | 775 | — | — | | | 1,280 |
| | 5 | 125 | 1,675 | 25 | — | — | | | 2,560 |
| GMT | | | | | | | | | 2,560 |
| ChimeriVax ™-WN04-C2 | 1 | 25 | 300 | — | — | — | 680 | 1.4 | 2,560 |
| | 2 | — | 775 | — | — | — | | | 2,560 |
| | 3 | — | 1,100 | — | — | — | | | 2,560 |
| | 4 | — | 775 | — | — | — | | | 2,560 |
| | 5 | — | 450 | — | — | — | | | 5,120 |
| GMT | | | | | | | | | 2,940 |
| ChimeriVax ™-WN04-dRS | 1 | 350 | 1,375 | — | — | — | 1,025 | 3 | >10,240 |
| | 2 | 175 | 1,375 | — | — | — | | | 1,280 |
| | 3 | — | — | — | 200 | 75 | | | 320 |
| | 4 | 75 | 850 | — | — | — | | | 5,120 |
| | 5 | 25 | 1,325 | — | — | — | | | 2,560 |
| GMT | | | | | | | | | 2,230 |
| ChimeriVax ™-WN04-d7 | 1 | — | — | 25 | — | — | 260 | 2.2 | 640 |
| | 2 | — | — | 525 | — | — | | | 1,280 |
| | 3 | — | 300 | 250 | — | — | | | 640 |
| | 4 | — | 400 | 125 | — | — | | | 640 |
| | 5 | — | 25 | 50 | — | — | | | 1,280 |
| GMT | | | | | | | | | 840 |
| ChimeriVax ™-WN04-dB | 1 | — | 325 | 75 | — | — | 355 | 2.2 | 2,560 |
| | 2 | — | 150 | 100 | — | — | | | 640 |
| | 3 | — | — | 875 | — | — | | | 1,280 |
| | 4 | — | 250 | 50 | — | — | | | 5,120 |
| | 5 | — | 175 | — | — | — | | | 2,560 |
| GMT | | | | | | | | | 1,940 |
| ChimeriVax ™-WN04-dC[4] | 1 | — | — | — | — | — | 15 (<25) | 0.4 | 320 |
| | 2 | — | — | — | — | — | | | 1,280 |
| | 3 | — | 50 | — | — | — | | | 320 |
| | 4 | — | 25 | — | — | — | | | 1,280 |
| | 5 | — | — | — | — | — | | | 1,280 |
| GMT | | | | | | | | | 735 |
| ChimeriVax ™-WN04-dD | 1 | — | — | 150 | — | — | 145 | 2 | 2,560 |
| | 2 | — | 300 | 125 | — | — | | | 640 |
| | 3 | — | — | — | — | — | | | 80 |
| | 4 | — | 200 | 75 | — | — | | | 2,560 |
| | 5 | — | 75 | 75 | — | — | | | 1,280 |
| GMT | | | | | | | | | 840 |
| ChimeriVax ™-WN04-E#3 | 1 | — | 1,150 | 100 | — | — | 1,460 | 2.6 | 640 |
| | 2 | — | 2,450 | 25 | — | — | | | 2,560 |
| | 3 | — | 1,325 | 75 | — | — | | | 640 |
| | 4 | — | 1,325 | 25 | — | — | | | 2,560 |
| | 5 | — | 1,050 | — | — | — | | | 640 |
| GMT | | | | | | | | | 1,110 |
| ChimeriVax ™-WN04-E#5 | 1 | 150 | 1,600 | — | — | — | 1,310 | 3 | 2,560 |
| | 2 | — | 750 | — | — | — | | | 2,560 |
| | 3 | 50 | 1,925 | — | — | — | | | 5,120 |
| | 4 | 25 | 1,650 | 225 | — | — | | | 1,280 |
| | 5 | — | 625 | 475 | — | — | | | 320 |

TABLE 5-continued

Viremia and antibody responses to ChimeriVax ™-WN04 variants
following SC inoculation of female Syrian hamsters

| Virus[1] | Hamster No. | Viremia, PFU/ml[2] | | | | | Mean peak viremia titer | Mean viremia duration (days) | PRNT$_{50}$ (day 30)[3] |
|---|---|---|---|---|---|---|---|---|---|
| | | Day 1 | Day 3 | Day 5 | Day 7 | Day 9 | | | |
| GMT | | | | | | | | | 1,690 |
| ChimeriVax ™-WN04-E#7 | 1 | — | 200 | 75 | — | — | 300 | 2.2 | 320 |
| | 2 | — | 325 | 150 | — | — | | | 80 |
| | 3 | — | 400 | 25 | — | — | | | 2,560 |
| | 4 | — | 525 | — | — | — | | | 640 |
| | 5 | — | — | 50 | — | — | | | 160 |
| GMT | | | | | | | | | 370 |
| ChimeriVax ™-WN04-E#6A | 1 | — | — | — | — | — | 30 | 2 | <10 |
| | 2 | — | — | — | — | 75 | | | 40 |
| | 2 | — | — | 75 | — | 25 | | | 80 |
| GMT | | | | | | | | | 32 |
| ChimeriVax ™-WN02 Large Plaque control | 1 | 50 | 2,425 | — | — | — | 2,285 | 2.2 | 5,120 |
| | 2 | — | 2,575 | — | — | — | | | 10,240 |
| | 3 | — | 2,925 | — | — | — | | | 5,120 |
| | 4 | — | 1,850 | 175 | — | — | | | 10,240 |
| | 5 | 75 | 1,650 | — | — | — | | | 5,120 |
| GMT | | | | | | | | | 6,760 |
| ChimeriVax ™-WN02 Small Plaque control | 1 | — | — | — | — | — | 5 (<25) | 0.2 | 80 |
| | 2 | — | — | — | — | — | | | 320 |
| | 3 | — | — | — | — | — | | | 40 |
| | 4 | — | — | — | — | — | | | <10 |
| | 5 | — | 25 | — | — | — | | | <10 |
| GMT | | | | | | | | | 16 |
| YF-VAX | 1 | — | — | Hamster lost | N/A | N/A | 0 (<25) | 0 | N/A |
| | 2 | — | — | — | — | — | | | 1,280 |
| | 3 | — | — | — | — | — | | | 5,120 |
| | 4 | — | — | — | — | — | | | 320 |
| | 5 | — | — | — | — | — | | | 10,240 |
| GMT | | | | | | | | | 2,150 |
| Mock | 1 | n.d. | n.d. | n.d. | n.d. | n.d. | N/A | N/A | <10 |
| | | | | | | | | | <10 |
| | 5 | n.d. | n.d. | n.d. | n.d. | n.d. | | | <10 |
| | | | | | | | | | <10 |
| | 3 | n.d. | n.d. | n.d. | n.d. | n.d. | | | <10 |
| | | | | | | | | | <10 |
| | 4 | n.d. | n.d. | n.d. | n.d. | n.d. | | | <10 |
| | | | | | | | | | <10 |
| | 5 | n.d. | n.d. | n.d. | n.d. | n.d. | | | <10 |
| | | | | | | | | | <10 |

[1]Inoculation volumes: 100 µl; inoculation doses: 5 log$_{10}$ pfu for ChimeriVax ™-WN04 viruses and WN02 LP and SP controls, and ~4 log$_{10}$ pfu for YF17D (YF-VAX); mock-inoculated animals received 100 µl of dilution medium (MEM, 50% FBS).
[2]Level of detection: 25 PFU/ml.
[3]Neutralizing antibody titers determined by PRNT$_{50}$ on day 30 against: ChimeriVax ™-WN02 for all groups inoculated with ChimeriVax ™-WN variants, or YF17D for YF-VAX group, or both for mock-inoculated group.
[4]In a separate hamster experiment, the Passage 5 (P5) sample of the dC mutant, in which the deletion spontaneously increased to 24 nucleotides (see text above), was tested. The virus remained highly attenuated (mean peak viremia 25 pfu/ml, mean duration 3.5 days) and immunogenic (PRNT$_{50}$ GMT of 452 on day 33). CS2d5 and CS2d16 P2 viruses were also tested and found similarly highly attenuated and immunogenic (mean peak viremia (pfu/ml)/mean viremia duration (days)/PRNT$_{50}$ GMT on day 33 of 137/2.75/127 and 343/2.25/905, respectively). All animals immunized with these WN04 variants including dC P5 were solidly protected, in contrast to the WN02 Small Plaque control, when challenged ~10 months post-immunization with wild type WN.

The ChimeriVax™-WN02 LP control (under-attenuated vaccine variant) induced high peak viremia in 5 inoculated hamsters ranging from 1,650 to 2,925 PFU/ml (mean 2,285 PFU/ml). These animals had the highest WN neutralizing antibody titers on day 30 in the range of 5,120-10,240 (GMT 6,760). The WN02 SP control induced no detectable viremia in 4 of 5 animals; a low level viremia detected in one hamster on day 3 was at the assay detection limit of 25 PFU/ml. WN-specific antibody response was very low in these animals. It was undetectable in two hamsters (titer<10); the other three had low antibody titers of 40-320. Interestingly, inoculation with YF-VAX resulted in no detectable viremia but a high YF-specific neutralizing antibody response (320-10,240 PRNT50 titers; GMT 2,150). As expected, mock-inoculated animals had no WN- or YF-specific neutralizing antibodies on day 30.

To achieve a minor reduction in viscerotropism for primates, we ideally wanted to identify in the hamster model a set of ChimeriVax™-WN04 variants causing a range of viremias that would be lower than that of the LP virus, but at the same time inducing a higher immune response than the SP virus. Of the 11 tested ChimeriVax™-WN04 viruses, most appeared to be at least somewhat attenuated in vivo compared to the LP virus (Table 5) as judged by post-inoculation viremia levels (mean peak viremia titers ranged from <25 to 1,460 pfu/ml). Among the less attenuated variants were the C-protein deletion mutant C1, the 3'UTR deletion mutant dRS, and WN04-E variants #3 and #5. These viruses induced high neutralizing antibody responses (GMT 1,110-2,560). One virus, the WN04-E variant #6A, was clearly over-attenuated as evidenced by both very low viremia and weak antibody response. Undoubtedly, the latter variant can be excluded from further testing in monkeys/humans. ChimeriVax™-WN04 candidates having particularly favorable characteristics are the capsid protein deletion mutant C2, the 3'UTR small-deletion mutants d7, dB, dC, and dD, and the E#7 variant. These viruses caused moderately to strongly reduced viremia in hamsters (mean peak viremia titers in the range of <25-680 PFU/ml), which nevertheless did not preclude a strong immune response (neutralizing antibody GMT 370-2, 940).

To demonstrate protective efficacy, all animals were challenged intraperitoneally on day 62 after immunization with $4 \times 10^5$ PFU of virulent wild type WN virus (strain NY382/99). All animals that had high titers of WN neutralizing antibodies (on day 30), specifically in groups WN04-C1, C2, dRS, d7, dB, dC, dD, E#3, E#5, E#7, and WN02 LP control (see in Table 5), were completely protected as judged by the absence of post-challenge viremia (measured in sera harvested on days 1, 3, 5, 7, and 9), weight loss, symptoms, or death. At least some of the animals in other groups, specifically E#6A, WN02 SP control, YF-VAX, and Mock, which did not have high WN neutralizing antibody titers, were not protected as judged by at least one of the above-noted parameters. There was a high viremia on days 1-5 (peak viremia titer of up to $9.75 \times 10^5$ pfu/ml) in all YF-VAX and mock-immunized animals. Most of these animals became sick, lost weight, and 2 animals in the YF-VAX group died. Two animals in the E#6 group and 1 animal in the WN02 SP group showed a low level viremia on days 1-2.

Figure 5:
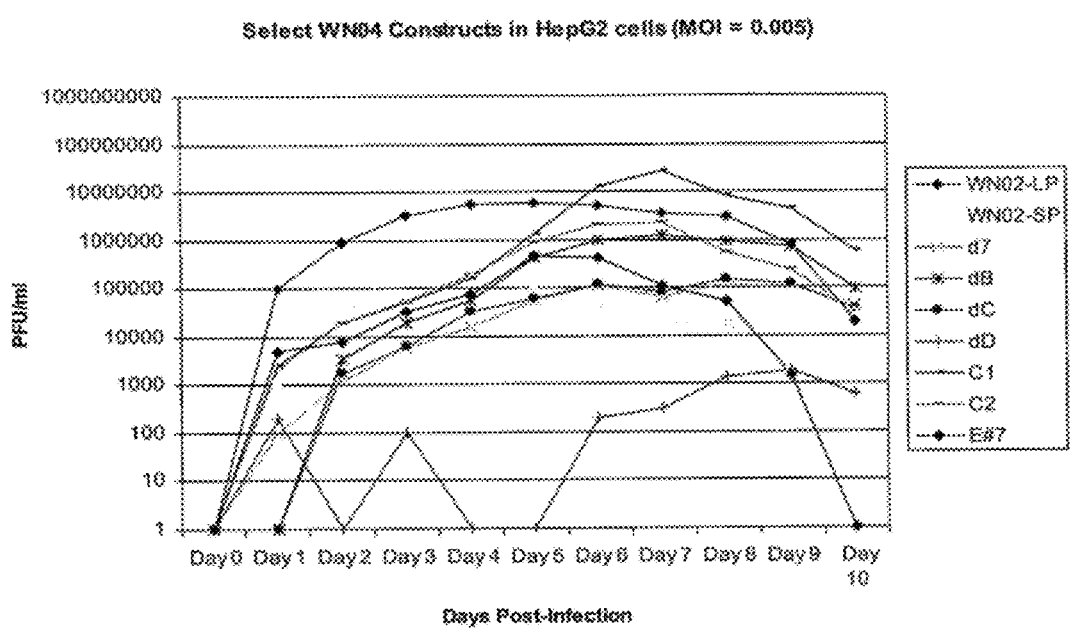
FIG. 5 is a graph showing the growth kinetics of selected ChimeriVax™-WN04 variants and WN02 Large Plaque (underattenuated vaccine) and Small Plaque controls.

Effects of Mutations in ChimeriVax™-WN04 Variants on Virus Growth in Hepatic Cells To obtain additional evidence of the reduced viscerotropism resulting from WN04 mutations, we analyzed growth kinetics of some of the most promising ChimeriVax™-WN04 variants (selected based on the data presented above, e.g., low viremia and high immunognicity in hamsters; see in Table 5) in human hepatoma cell line HepG2. As YF virus is a hepatotropic virus, we hoped to see a reduction in replication of WN04 variants compared to ChimeriVax™-WN02 LP virus (underattenuated vaccine). Monolayers of HepG2 cells were infected at an MOI of 0.005 PFU/ml, aliquots of virus-containing supernatants were harvested daily (up to day 10), and virus titers were then determined by plaque assay in Vero cells. The attenuated WN04 variants included in this experiment were the 3'UTR deletion mutants d7, dB, dC, and dD, capsid protein deletion mutant C2 (as well as the less attenuated mutant C1 as an additional control), and the envelope protein mutant E#7. Except for the C1 mutant, all other WN04 viruses replicated less efficiently as compared to WN02 LP virus (FIG. 5), but most of them (with the exception of dD) grew better than the WN02 SP variant, which is presumed to be an overattenuated vaccine variant for humans. This indicated that some WN04 mutations can reduce hepatotropism of the vaccine in humans, which is a highly desirable feature. This experiment further shows the benefits of candidates to E#7, d7, dC, and dD exhibiting the most clear reduction in replication compared to WN02 LP, with the dD mutant perhaps being the least hepatotropic.

ChimeriVax™-WN04 Double Mutants; Analysis of Viscerotropism and Immunogenicity in Hamsters Combining different types of attenuating mutations should result in additional attenuation and a more reliable vaccine phenotype, less likely to revert to pathogenicity. To this end, four double-mutant ChimeriVax™-WN04 variants were produced in which the C2 deletion was combined with d7, dB, or dD 3'UTR deletions or the E#5 combination of mutations in the envelope proteins (additional E176, 177, and 280 SA14-14-2-specific changes). DNA templates for in vitro transcription were obtained by standard two- or three-fragment ligation using appropriate portions of 5'3' and 5.2 plasmids previously constructed for WN04 single mutants. These were transcribed with SP6 RNA polymerase and viruses were recovered following electroporation of Vero cells with the RNA transcripts. P2 viruses were titrated in Vero cells. All four double mutants appeared strongly attenuated in cell culture as they produced tiny plaques, smaller than those of WN02 LP and SP controls. The C2+E5 mutant had a high titer of $1.3 \times 10^7$ pfu/ml, while the other three viruses (C2+d7, C2+dB, and C2+dD) had intermediate titers of $4.2-6.1 \times 10^5$ pfu/ml (Table 6).

TABLE 6

In vitro characteristics of ChimeriVax ™-WN04 double mutants

| Virus | P2 titer, PFU/ml | Plaque morphology on day 5 |
|---|---|---|
| C2 + E5 P2 | $1.3 \times 10^7$ | tiny (average ~0.5 mm) |
| C2 + d7 P2 | $4.2 \times 10^5$ | tiny |
| C2 + dB P2 | $6.1 \times 10^5$ | tiny |
| C2 + dD P2 | $6.1 \times 10^5$ | tiny |
| WN02 LP control | $9 \times 10^6$ | large/small, clear |
| WN02 SP control | $5.8 \times 10^7$ | small, clear |

To evaluate attenuation and immunogenicity, four-week old female Syrian hamsters were inoculated sub-cutaneously (SC) with 5 $\log_{10}$ pfu of the double mutants, as well as WN02 LP and SP control viruses, or diluent (sham). Viremia was measured on days 1-10 and antibody responses were determined on day 35 by $PRNT_{50}$. The results are shown in Table 7. The four double mutants were replication competent, causing detectable low-level viremia in most animals, except for C2+d7 for which viremia was detected only in one animal. These viruses were significantly more attenuated as compared to the WN02 LP virus (mean peak viremia ~7,000 pfu/ml), and appeared more attenuated compared to the corresponding single mutants (e.g., compare mean peak viremia titers with those in Table 5). Although viremia was not detected in every animal, all hamsters developed high-level neutralizing antibody response. The $PRNT_{50}$ GMT values for C2+E5, C2+d7, C2+dB, and C2+dD were 1:640, 1:840, 1:1, 280, and 1:640, respectively.

TABLE 7

Viremia and antibody responses to ChimeriVax ™-WN04 double mutant variants following SC inoculation of female Syrian hamsters.

| Virus | Hamsster # | Viremia titer (pfu/ml) on days[1] | | | | | | | Mean peak viremia titer | Mean viremia duration (days) | $PRNT_{50}$ (on day 35) |
| | | d1 | d2 | d3 | d4 | d5 | d6 | d7 | | | |
|---|---|---|---|---|---|---|---|---|---|---|---|
| C2 + E5 P2 | 1 | — | — | — | 600 | 1,300. | 800 | 1,850 | 810 | 3.0 | 640 |
| | 2 | 50 | — | — | — | 50 | 600 | 1,200 | | | 640 |
| | 3 | — | — | — | 50 | 50 | — | — | | | 640 |
| | 4 | 50 | — | 500 | 200 | — | — | — | | | 1,280 |
| | 5 | — | — | — | 450 | 50 | — | — | | | 320 |

TABLE 7-continued

Viremia and antibody responses to ChimeriVax ™-WN04 double mutant variants following SC inoculation of female Syrian hamsters.

| Virus | Hamsster # | d1 | d2 | d3 | d4 | d5 | d6 | d7 | Mean peak viremia titer | Mean viremia duration (days) | PRNT$_{50}$ (on day 35) |
|---|---|---|---|---|---|---|---|---|---|---|---|
| GMT | | | | | | | | | | | 640 |
| C2 + d7 P2 | 1 | — | — | 50 | — | — | — | — | 10 | 0.2 | >1,280 |
| | 2 | — | — | — | — | — | — | — | | | 640 |
| | 3 | — | — | — | — | — | — | — | | | 320 |
| | 4 | — | — | — | — | — | — | — | | | 1,280 |
| | 5 | — | — | — | — | — | — | — | | | 1,280 |
| GMT | | | | | | | | | | | 840 |
| C2 + dB P2 | 1 | — | — | — | — | — | — | — | 230 | 1.6 | >1,280 |
| | 2 | — | — | 200 | 50 | — | — | — | | | 1,280 |
| | 3 | — | — | 200 | 300 | — | — | — | | | 1,280 |
| | 4 | — | — | 50 | 600 | 50 | — | — | | | >1,280 |
| | 5 | — | — | 50 | — | — | — | — | | | 1,280 |
| GMT | | | | | | | | | | | 1,280 |
| C2 + dD P2 | 1 | — | — | — | — | — | — | — | 80 | 1.0 | 1,280 |
| | 2 | — | 100 | 250 | — | — | — | — | | | 1,280 |
| | 3 | — | 50 | — | — | — | — | — | | | >1,280 |
| | 4 | — | 50 | — | — | — | — | — | | | >1,280 |
| | 5 | — | 50 | — | — | — | — | — | | | 160 |
| GMT | | | | | | | | | | | 640 |
| WN02 SP | 1 | — | 50 | — | — | — | — | — | 10 | 0.2 | 320 |
| | 2 | — | — | — | — | — | — | — | | | 320 |
| | 3 | — | — | — | — | — | — | — | | | 40 |
| | 4 | — | — | — | — | — | — | — | | | 320 |
| | 5 | — | — | — | — | — | — | — | | | 40 |
| GMT | | | | | | | | | | | 140 |
| WN02 LP | 1 | — | 700 | 3,750 | 1,350 | — | — | — | 7,070 | 3.6 | >320 |
| | 2 | 2,450 | 20,000 | 7,600 | 50 | — | — | — | | | >640 |
| | 3 | — | 50 | 550 | 5,800 | 3,400 | — | — | | | >320 |
| | 4 | — | 400 | 2,050 | 2,900 | — | — | — | | | >640 |
| | 5 | — | 200 | 450 | 2,900 | 150 | — | — | | | >640 |
| GMT | | | | | | | | | | | >485[2] |

[1]Viremia detection limit 50 pfu/ml; days 8-10 were also tested, no viremia detected.
[2]Because serum dilution producing 50% neutralization was not reached for all animals, this value may be significantly higher than shown.

To demonstrate protection, animals were challenged intraperitoneally on day 36 with a highly lethal wild type WN virus, strain NY385/99, which is more pathogenic than NY382/99 used in experiments above, at 2×10$^5$ pfu/dose. Animals immunized with WN04 double-mutants, as well as WN02 LP control, were completely protected, as there was no post-challenge viremia (measured on days 2, 4, and 6) and no weight loss that would be indicative of disease. In contrast, WN02 SP and sham immunized control animals were not protected. They developed viremia (peak titers of 250-3,000 and >2,000 pfu/ml for WN02 SP and sham animals, respectively), showed symptoms of disease, and lost weight. One of 5 and 4 of 5 animals in WN02 SP and sham groups, respectively, died. Two survived animals in WN02 SP group and 1 survived animal in sham group were paralyzed).

We have thus successfully generated multiple ChimeriVax™-WN04 candidates that are more attenuated as compared to the previous ChimeriVax™-WN02 vaccine, but not over-attenuated, by using unique modifications of three different methods for flavivirus attenuation, and introduction of different types of attenuating mutations singly or in combinations.

What is claimed is:

1. A chimeric flavivirus comprising a yellow fever virus in which the yellow fever virus membrane and envelope proteins have been replaced with the membrane and envelope proteins of a West Nile virus, wherein the West Nile virus envelope protein comprises substitutions in amino acid positions 107, 316, and 440, and the chimeric flavivirus further comprises two or more mutations selected from the group consisting of: (a) a deletion in 3' untranslated region sequences that comprises less than 30 nucleotides, (b) a deletion in capsid protein sequences, and (c) one or more additional substitutions in the West Nile virus envelope protein at amino acid positions 138, 176, 177, or 280.

2. The chimeric flavivirus of claim 1, wherein the yellow fever virus is YF17D.

3. A chimeric flavivirus comprising a yellow fever virus in which the yellow fever virus membrane and envelope proteins have been replaced with the membrane and envelope proteins of a West Nile virus, wherein the West Nile virus envelope protein comprises substitutions in amino acid positions 107, 316, and 440, and the chimeric flavivirus further comprises two or more mutations selected from the group consisting of: (a) a deletion in 3' untranslated region sequences that destabilizes a stem structure in the 3' untranslated region of the virus, (b) a deletion in capsid protein sequences, and (c) one or more additional substitutions in the West Nile virus envelope protein at amino acid positions 138, 176, 177, or 280.

4. The chimeric flavivirus of claim 3, wherein the stem structure is in a non-conserved region of the 3' untranslated region of the virus.

5. The chimeric flavivirus of claim 1, wherein the deletion is selected from the group consisting of dRS, d7, dA, dB, dC, dD, CS2d5, CS2d16, and dC-P5.

6. The chimeric flavivirus of claim 1, wherein the deletion comprises one or more nucleotides of conserved sequence 2 (CS2).

7. A method of inhibiting flavivirus infection in a subject, the method comprising administering to the subject a composition comprising the chimeric flavivirus of claim 1.

8. A pharmaceutical composition comprising the chimeric flavivirus of claim 1.

9. A nucleic acid molecule comprising the genome of the chimeric flavivirus of claim 1.

10. The chimeric flavivirus of claim 1, wherein the chimeric flavivirus comprises a deletion of 1-3 amino acids of the capsid protein.

11. The chimeric flavivirus of claim 10, wherein the deletion comprises amino acids of Helix I of the capsid protein.

12. The chimeric flavivirus of claim 10, wherein the deletion is C2.

13. The chimeric flavivirus of claim 1, wherein said chimeric flavivirus comprises capsid protein deletion C2 in combination with
  (1) a 3' untranslated region deletion selected from the group consisting of (a) d7, (b) dB, and (c) dD; and
  (2) a West Nile virus envelope protein substitution at an amino acid position selected from the group consisting of 176, 177, and 280.

14. The chimeric flavivirus of claim 1, wherein said substitutions at amino acid positions 107, 316, and 440 are L to F, A to V, and K to R, respectively.

15. The chimeric flavivirus of claim 1, wherein said substitutions in the West Nile virus envelope protein at amino acid positions 138, 176, 177, or 280 are E to K, Y to V, T to A, and K to M, respectively.

16. A method of inhibiting flavivirus infection in a subject, the method comprising administering to the subject a composition comprising the chimeric flavivirus of claim 3.

17. A pharmaceutical composition comprising the chimeric flavivirus of claim 3.

18. A nucleic acid molecule comprising the genome of the chimeric flavivirus of claim 3.

19. The chimeric flavivirus of claim 3, wherein the chimeric flavivirus comprises a deletion of 1-3 amino acids of the capsid protein.

* * * * *